(12) United States Patent
Becker et al.

(10) Patent No.: US 9,315,537 B2
(45) Date of Patent: Apr. 19, 2016

(54) MULTIPLE ORTHOGONAL LABELLING OF OLIGONUCLEOTIDES

(75) Inventors: Juliane Becker, Mannheim (DE); Andres Jäschke, Heidelberg (DE); Ayan Samanta, Mannheim (DE); Manfred Wiessler, Frankenthal (DE)

(73) Assignees: DEUTSCHES KREBSFORSCHUNGSZENTRUM, Heidelberg (DE); RUPRECHT-KARLS-UNIVERSITAT HEIDELBERG, Heidelberg (DE)

( * ) Notice: Subject to any disclaimer, the term of this patent is extended or adjusted under 35 U.S.C. 154(b) by 24 days.

(21) Appl. No.: 14/342,021

(22) PCT Filed: Aug. 31, 2012

(86) PCT No.: PCT/EP2012/003666
§ 371 (c)(1),
(2), (4) Date: Jul. 30, 2014

(87) PCT Pub. No.: WO2013/029801
PCT Pub. Date: Mar. 7, 2013

(65) Prior Publication Data
US 2015/0218203 A1 Aug. 6, 2015

(30) Foreign Application Priority Data
Sep. 2, 2011 (EP) .................................. 11007142

(51) Int. Cl.
*C07H 19/04* (2006.01)
*C07H 21/00* (2006.01)
(52) U.S. Cl.
CPC ...................................... *C07H 21/00* (2013.01)
(58) Field of Classification Search
CPC .................................................. C07H 21/00
USPC ....................................................... 536/26.6
See application file for complete search history.

(56) References Cited

FOREIGN PATENT DOCUMENTS

EP          11175266          7/2011
WO      WO 2011/095336      8/2011

OTHER PUBLICATIONS

Gramlich, Philipp M E et al: "Click Click Click: Single to Triple Modification of DNA", Angewandte Chemie. International Edition, Wi Ley VCH Verlag, Weinheim, vol. 47, No. 18, Jan. 1, 2008, pp. 3442-3444.
Paredes, Eduardo et al: "Click Chemistry for Rapid Labeling and Ligation of RNA", Chembiochem, vol. 12, No. 1, Jan. 3, 2011, pp. 125-131.
Weisbrod, Samuel H. et al: "Novel strategies for the site-specific covalent labelling of nucleic acids", Chemical Communications, No. 44, Jan. 1, 2008, p. 5675.
Koizumi, M. et al., Nucleic Acids Res., 1989,17:7059-7071.
Venkatesan, N. et al., Curr. Med. Chem., 2003, 10:1973-1991.
Beaucage, S.L. and Lyer, P.R., Tetrahedron, 1993: 6123-6194.
Omumi, A. et al., J. Am. Chem. Soc. 2011,133: 42-50.
Sauer, J. and Lang, D., Angew. Chem. 1964, 76: 603.
Sauer, J. et al., Chem. Ber., 1965, 98: 1435-1445.
Seelig, B. et al.,Tetrahedron Lett. 1997, 38: 7729-7732.
Seelig, B. and Jaschke, A., Chem. Biol. 1999, 6: 167-176.
Deng, X. et al., Angew. Chem. Int. Ed. 2011, 50: 6522-6526.
Braun K. et al., Drug Des. Dev. Ther. 2008, 2: 289-301.
Pipkorn, R. et al., J. Pept. Sci. 2009, 15: 235-241.
Best, M., Biochemistry, 2009, 48:6571-6584.
Huisgen, R., Proc. Chem. Soc. London, 1961, 357.
baseclick.eu/products.php?search num str=BCA-03, ©2011.
Taylor, M. T.; Blackman, M. L.; Dmitrenko, O.; Fox, J. M., J. Am. Chem. Soc. 2011, 133, 9646-9.
Sauer, J., et al., Eur. J. Org. Chem. 1998: 2885-2896.
International Search Report and Written Opinion in corresponding PCT Application No. PCT/EP2012/003666, mailed Nov. 27, 2012.

*Primary Examiner* — Jezia Riley
(74) *Attorney, Agent, or Firm* — Leason Ellis LLP.

(57) ABSTRACT

In summary, the present invention concerns a method for multiple orthogonal labelling of oligonucleotides, preferably RNA or DNA, by simultaneously performing the inverse Diels-Alder reaction (DAinv) and the copper-catalyzed click reaction (CuAAC), wherein the method is employed in a single step by just adding the different reaction components together and incubating the aqueous reaction mixture preferably for one hour at room temperature. In detail, the reaction components are one or more $N_3$-modified labels, a copper compound, a stabilizing ligand, a reducing agent and one or more electron-deficient label-modified dienes that are added together with an at least double-modified oligonucleotide having one more nucleotides containing one or more N3-reactive groups and one or more electron-rich dienophiles, wherein a terminal alkyne moiety is preferably used as N3-reactive group(s) and a frans-cyclooctene moiety or norbornene is preferably used as electron-rich dienophile(s), more preferably frans-cyclooctene. Therefore, the present invention provides a one-pot method for post-synthetic multiple orthogonal labeling of oligonucleotides, which allows the site-specific introduction of more than one label, preferably of at least two labels into oligonucleotides after solid-phase synthesis, wherein the DAinv takes place on the dienophile modification only and the CuAAC selectively takes place on the N3-reactive group modification.

26 Claims, 15 Drawing Sheets

$R^1 / R^2$ = aryl / heteroaryl

*Fig. 3*
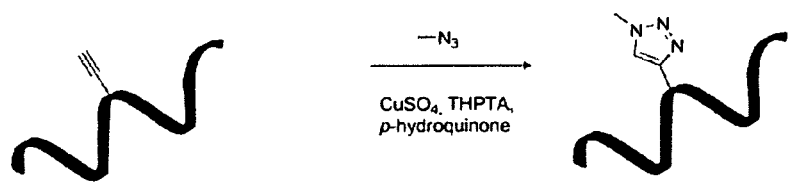
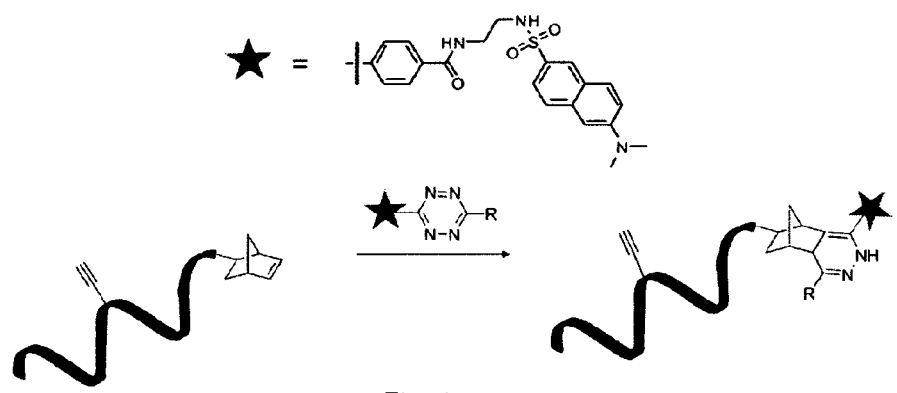
*Fig. 4*
*Fig. 5*
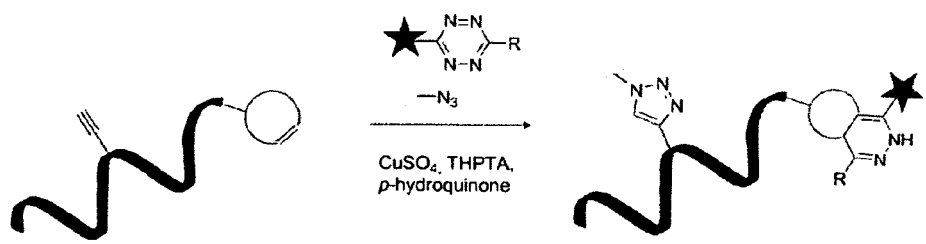

MULTIPLE ORTHOGONAL LABELLING OF OLIGONUCLEOTIDES

CROSS-REFERENCE TO RELATED PATENT APPLICATIONS

This application is a U.S. National Phase Application under 35 U.S.C. §371 of International Patent Application No. PCT/EP2012/003666, filed Aug. 31, 2012, and claims the priority of European Patent Application No. 11007142.0, filed Sep. 2, 2011, all of which are incorporated by reference in their entireties. The International Application was published in Germany on Mar. 7, 2013 as International Publication No. WO 2013/029801 under PCT Article 21(2).

TECHNICAL FIELD

The present invention concerns a method for multiple orthogonal labelling of oligonucleotides, preferably RNA or DNA, by simultaneously performing an inverse Diels-Alder reaction and a copper-catalyzed click reaction.

PRIOR ART

Labelling of oligonucleotides with fluorescent dyes or affinity tags is gaining importance in nanotechnology and modern life sciences (Weisbrod, S. H. and Marx, A., Chem. Commun. 2008: 5675-5685), wherein the incorporation of chemical modifications for their labeling can be achieved via chemical synthesis, enzymatic synthesis or synthesis in the organism. With regard to the chemical synthesis, the phosphoramidite method as a solid-phase synthesis method is used most widely at present (Koizumi, M. et al., Nucleic Acids Res., 1989, 17:7059-7071; Venkatesan, N. et al., Curr. Med. Chem., 2003, 10:1973-1991). Therefore, either phosphoramidites or solid supports carrying the respective modification have to be prepared and incorporated (Beaucage, S. L. and Lyer, P. R., Tetrahedron, 1993: 6123-6194). The method makes use of a condensation reaction between a nucleoside phosphoramidite and a nucleoside as a key reaction using imidazole- or tetrazole-based chemical compounds as activators. The disadvantage of this method is the fact that the harsh conditions during solid-phase synthesis, however, enables the direct incorporation of only a small subset of chemical modifications in oligonucleotides during their synthesis because of the instability of many functional groups towards standard phosphoramidite coupling, oxidizing and deprotection conditions. However, these limitations can be overcome by using post-synthetic labelling strategies that introduce modifications after solid-phase synthesis (Weisbrod, S. H. and Marx, A., Chem. Commun. 2008: 5675-5685; Omumi, A. et al., J. Am. Chem. Soc. 2011, 133: 42-50). Preferably, they are bioorthogonal and do work efficiently under mild conditions.

There are several methods in the prior art for the post-synthetic labelling in order to introduce modifications after solid-phase synthesis of oligonucleotides, wherein a long-standing interest exists in cycloadditions as labelling strategies for biomolecules. For example, in PCT/EP2011/000491 the inventors developed a post-synthetic bioorthogonal cycloaddition reaction for labelling oligonucleotides, which is based on a Diels-Alder reaction with inverse electron-demand (DAinv). Such highly selective and efficient cycloaddition reaction takes place between an electron-rich dienophile and an electron-deficient diene (Sauer, J. and Lang, D., Angew. Chem. 1964, 76: 603; Sauer, J. et al., Chem. Ber., 1965, 98: 1435-1445). In detail, the method is characterized by the introduction of norbornene or trans-cyclooctene moieties into oligonucleotides at various positions, which are reactive in inverse Diels-Alder reactions, wherein after cleavage from the resin and deprotection, inverse Diels-Alder reactions are conducted using water-stable tetrazines. While former Diels-Alder reactions using anthracene-modified oligonucleotides and maleimide as dienophile required huge (>500-fold) excess of dienophile for appreciable product formation (Seelig, B. et al., Tetrahedron Lett. 1997, 38: 7729-7732; Seelig, B. and Jaschke, A., Chem. Biol. 1999, 6: 167-176), the method as disclosed in PCT/EP2011/000491 showed a dramatically improved reaction rate.

Furthermore, EP 11 175 266.3 is directed to a method for the post-synthetic incorporation of chemical modifications into RNA oligonucleotides for their labelling, which is based on the enzymatic incorporation of a small functional group that is further converted in a subsequent chemical reaction in which the label of choice can be attached. In detail, the inventors developed a two-step method, wherein in a first step, the RNA oligonucleotide is tailed by the incorporation of a convertible azido-modified ($N_3$-modified) nucleotide at the 3'-terminus in an enzymatic reaction with a nucleotidyl transferase, e.g. the enzyme poly(A) polymerase (PAP) and an $N_3$-modified nucleoside triphosphate ($N_3$-modified NTP), and in a second step, the functionalization is accomplished with an azide-reactive group ($N_3$-reactive group), e.g. via a copper-catalyzed 1,3-dipolar cycloaddition reaction between the incorporated $N_3$-modified nucleotide and a functional group containing a terminal alkyne moiety (copper-catalyzed click reaction, CuAAC), via a strain-promoted [3+2] dipolar cycloaddition between the incorporated $N_3$-modified nucleotide and a functional group containing a cyclooctyne moiety (strain-promoted click reaction), or via an azide-phosphine conjugation between the incorporated $N_3$-modified nucleotide and a functional group containing a phosphine moiety (Staudinger ligation). To achieve internal chemical modifications or rather functionalization of RNA oligonucleotides, an additional step can be introduced between the first and the second step, in which a second RNA oligonucleotide is enzymatically attached to the $N_3$-modified nucleotide at the 3'-terminus of the first step, thus converting the 3'-terminal $N_3$-modified nucleotide into an internal $N_3$-modified nucleotide that can be further converted in one of the aforementioned reactions.

For some applications, however, multiple orthogonal labelling, such as dual orthogonal labelling, with different modifications is required, for example for FRET (fluorescence resonance energy transfer) measurements. Therefore, some of the labelling reactions of the prior art offer the possibility to simultaneously introduce more than one label, e.g. by using the cycloaddition reaction to two dienophile units in the oligonucleotide as disclosed in PCT/EP2011/000491 or by incorporating more than one $N_3$-modified nucleotide into the RNA oligonucleotide as disclosed in EP 11 175 266.3. However, the multiple orthogonal labelling with different modifications is usually done stepwise, i.e. in multiple labelling steps, in order to circumvent any unwanted side reactions between coupling partners with different reactivities as observed in the simultaneous methods. One attempt works over the protection of one reaction partner during the first labelling step and performance of a second labelling step after deprotection (Gramlich, P. M. E. et al., Angew. Chem. 2008, 47: 3442-3444). Another strategy is based on stepwise labelling of an alkyne with different reactivities, e.g. by using two different azide building blocks (Deng, X. et al., Angew. Chem. Int. Ed. 2011, 50: 6522-6526).

However, all of the current technologies, i.e. the simultaneous and stepwise methods for multiple orthogonal labelling of oligonucleotides by incorporating at least two different chemical modifications are not practical, since there are the following disadvantages:
(1) In the current simultaneous methods, the coupling partners interact with each other so that unwanted side reactions occur.
(2) As the labelling reactions are not simultaneously performed in the stepwise methods, the stepwise methods are more time-consuming than a simultaneous strategy.
(3) As current stepwise methods are mostly connected with purification steps between each labelling step, the stepwise methods are more time-consuming than a simultaneous strategy.
(4) In addition, every purification step decreases the amount of the finally double labelled product in the stepwise methods.
(5) Moreover, some of the stepwise labelling approaches require building blocks, so that the synthesis of which is rather demanding.

SUMMARY OF THE INVENTION

Since the aforementioned technologies have several disadvantages for the post-synthetic multiple orthogonal labelling of oligonucleotides, there is a further need for a method, which solves the technical problems as described above. Thus, the present invention was made in view of the prior art described above, and the object of the present invention is to provide a fast method for post-synthetic multiple orthogonal labelling of oligonucleotides, which does not show unwanted side reactions and a decreasing amount of the finally labelled product due to purification steps.

To solve the problems, the present invention provides a selective and simultaneous method for post-synthetic multiple orthogonal labelling of oligonucleotides, preferably RNA or DNA, by simultaneously performing the inverse Diels-Alder reaction (DAinv) and the copper-catalyzed click reaction (CuAAC), wherein the method is employed in a single step by just adding the different reaction components together and incubating the aqueous reaction mixture preferably for one hour at room temperature. In detail, the reaction components are one or more $N_3$-modified labels, a copper compound, a stabilizing ligand, a reducing agent and one or more electron-deficient label-modified dienes that are added together with an at least double-modified oligonucleotide having one or more nucleotides containing one or more $N_3$-reactive groups and one or more electron-rich dienophiles, wherein a terminal alkyne moiety is preferably used as $N_3$-reactive group(s) and a trans-cyclooctene moiety or norbornene is preferably used as electron-rich dienophile(s), more preferably trans-cyclooctene. Therefore, the present invention provides a one-pot method for post-synthetic multiple orthogonal labeling of oligonucleotides, which allows the site-specific introduction of more than one label, preferably of at least two labels into oligonucleotides after solid-phase synthesis, wherein the DAinv takes place on the dienophile modification only and the CuAAC selectively takes place on the $N_3$-reactive group modification.

BRIEF DESCRIPTION OF THE FIGURES

FIG. 3 shows one reaction of the dual orthogonal labeling method of the present invention wherein oligonucleotide strands carrying a terminal alkyne moiety undergo copper catalyzed click-reaction with an $N_3$-modified functional group.

FIG. 4 shows the one-pot reaction for multiple orthogonal labelling of oligonucleotides.

FIG. 5 shows the DAinv reaction on a double-modified oligonucleotide.

FIG. 10 shows the MS spectra of the double-modified oligonucloetides ODN1a and ODN2a.

FIG. 11 shows the MSMS spectrum for the double-modified oligonucleotide ODN1a.

FIG. 12 shows the detailed MSMS spectrum for the double modified oligonucleotide ODN1a.

DETAILED DESCRIPTION OF THE INVENTION

Figure 1:
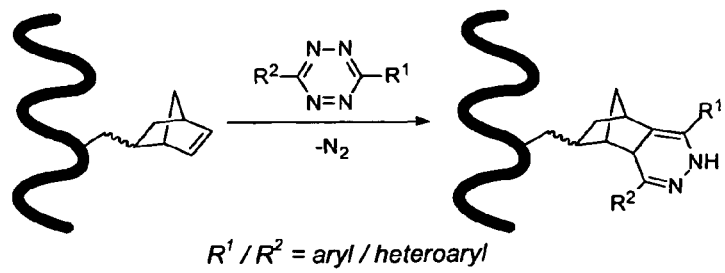
FIG. 1 shows one reaction of the multiple orthogonal labelling method of the present invention, wherein oligonucleotide strands carrying an electron-rich dienophile undergo DAinv reaction with an electron-deficient label-modified diene.

The present invention concerns a method for post-synthetic multiple orthogonal labelling of oligonucleotides by simultaneously performing an "inverse Diels-Alder reaction" (DAinv) and a "copper-catalyzed click reaction" (CuAAC).

The term "multiple" of "multiple orthogonal labelling" as used in the present invention means that the oligonucleotides of the present invention are labelled with more than one label, i.e. with at least two labels.

"Labelling" of the present invention comprises fluorescent labelling and radioactive labelling, wherein "labels" according to the present invention are molecules containing "functional groups" that are specific groups of atoms that are responsible for the characteristic chemical reaction of those molecules, e.g. fluorophores, which causes a molecule to be fluorescent. Thus, "fluorescent labelling" is the method of covalently attaching a fluorophore to another molecule, such as protein or nucleic acid, wherein in "radioactive labelling" radiolabels, i.e. substances containing a radioisotope are used.

"Labels" according to the present invention may be selected from the group consisting of pharmaceutical, therapeutical or diagnostic compounds such as dyes, radiolabels or affinity tags. The dyes may be selected from the group consisting of fluorescent, luminescent or phosphorescent dyes such as dansyl, fluorescein, acridine, rhodamine, BODIPY and cyanine dyes. Examples of affinity tags are biotin, the His-tag, the Flag-tag, the strep-tag, sugars, lipids, sterols, PEG-linkers, and co-factors that may be used to influence oligonucleotide properties like solubility, membrane permeability, and localization. Furthermore, a number of different radioactive forms of hydrogen, carbon, phosphorous, sulphur, and iodine may be used as radiolabels, including tritium, carbon-11, carbon-14, phosphorous-32, phosphorous-33, sulphur-33, iodine-123, and iodine-125.

The "oligonucleotide" of the present invention may have any length between 3 and 10000 nucleotides, preferably between 4 and 5000 nucleotides, more preferably between 5 and 1000 nucleotides or between 10 and 500 nucleotides, most preferably between 10 and 200 nucleotides. Thus, the method for multiple orthogonal labelling of the present invention may be performed with "shorter" or "longer" oligonucleotides, wherein the shorter oligonucleotides may have 4-8 nucleotides, preferably 7 and the longer oligonucleotides may have 15-300, preferably 18-300 nucleotides, preferably 19 nucleotides. Moreover, the oligonucleotide according to the present invention may be a single-stranded or double-stranded DNA or RNA molecule as well as a nucleic acid analog (e.g. PNA, LNA) or chimera of these with DNA and/or RNA. In addition, enzymatically modified PCR products may be used. It is an advantage of the present invention that such large molecules of nucleic acids can be modified by the method of the invention. Furthermore, the method of the present invention is performed by using shorter or longer oligonucleotides in a final concentration of about 0.5-15 µM.

According to the method of the present invention, one of the labelling reactions is the DAinv reaction between an electron-rich dienophile that is incorporated into an oligonucleotide (dienophile-modified oligonucleotide) via solid-phase synthesis and an electron-deficient diene that is modified with one or more labels (label-modified diene) so that the electron-rich dienophile of the oligonucleotide is further converted by the DAinv reaction in which the label of choice can be attached.

In a preferable embodiment of the method of the present invention, the DAinv reaction is performed according to method as described PCT/EP2011/000491 so that the DAinv reaction of the present invention comprises the following steps, which are consecutively performed (FIG. 1):

(a) Providing of an oligonucleotide modified by the incorporation of one or more electron-rich dienophile(s) (dienophile-modified oligonucleotide), wherein the oligonucleotide may be modified either single or multiple and either terminally (3' or 5') or internally.

(b) Providing of a label-modified diene, i.e. of an electron-deficient diene that is modified with one or more labels (label-modified diene).

(c) Reaction of the electron-rich dienophile(s) of step (a) with the label-modified diene via DAinv reaction.

$R^1$ and $R^2$ of FIG. 1 may be the same or different.

"Aryl" of FIG. 1 means any aromatic monocyclic or multicyclic ring system with 6 to 14 carbon atoms, preferably 6 to 10 carbon atoms. The aryl groups may be substituted with one or more substituents (e.g. $C_1$-$C_{12}$ alkyl, OH, halogen, etc.). Preferred aryl groups are phenyl or naphthyl.

"Heteroaryl" of FIG. 1 means any aromatic monocyclic or multicyclic ring system with 5 to 14 ring atoms wherein one or more ring atoms are different from C, e.g. N, S or O. Preferred heteroaryls are pyridyl, pyrazinyl, thienyl or, furanyl.

Figure 2:
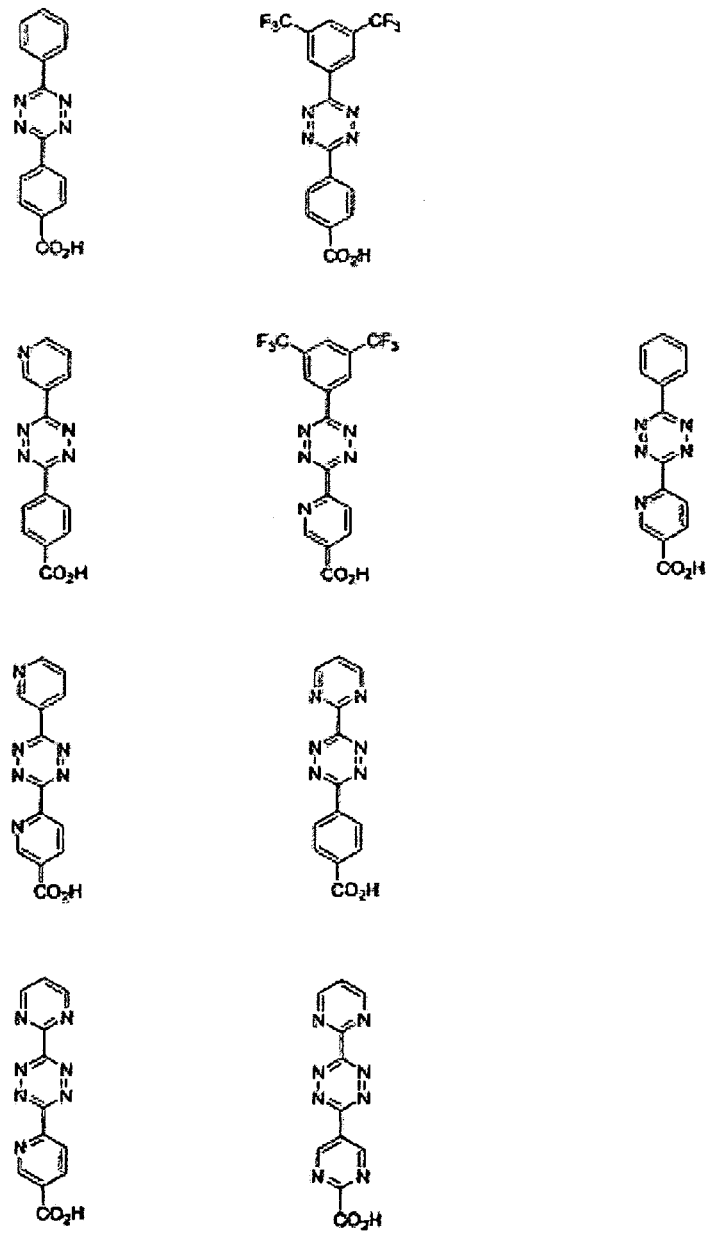
FIG. 2 shows the tetrazine compounds.

The "electron-rich dienophile" or rather "dienophile" of the method of the present invention may be a norbornene or a trans-cyclooctene moiety which preferably does not contain a terminal double bond, wherein the "electron-deficient label-modified diene" or rather "label-modified diene" may be an electron-deficient tetrazine or rather tetrazine that is modified, e.g. substituted with one or more labels. In a preferable embodiment any tetrazine known by a person skilled in the art may be used in the DAinv reaction, wherein examples of suitable tetrazines are shown in FIG. 2.

With regard to step (a) of the DAinv reaction, the dienophile-modified oligonucleotide is provided after incorporating electron-rich dienophile(s) via solid-phase synthesis into an oligonucleotide, preferably using Iodine or rather $^{tert}$butylhydroperoxide as oxidizing agent. In a preferred embodiment, norbornene phosphoramidite 1 was synthesized starting form bicyclo[2.2.1]hept-2-en-2-carbaldehyde for the selective modification of the 5'-terminus of an oligonucleotide. As another building block for 5'-modification, trans-cyclooctene phosphoramidite 3 was synthesized over isomerisation and phosphoramidite synthesis starting from cis-cyclooctenol. In further preferred embodiments, phosphoramidite 8 served as building blocks for internal modification of DNA. The preparation of phoshoramidites 1 and 3 is shown in the below examples. Phosphoramidite 8 is prepared according to Gutsmiedl, K. et al. (Org. Lett. 2009, 11: 2405-2408). Solid support 9, prepared by standard procedures, finally allowed selective 3'-derivatization: According to the present invention, the "solid support" may be any suitable support material or matrix, e.g. glass (particularly glass beads), sheets or membranes of polypropylene, nylon, cellulose, cellulose derivatives, polyether sulfones, polyamides, PVC, PVDF, polyester, Teflon, or polyethylene, preferably controlled pore glass (CPG). The solid support may be derivatized with functional groups, e.g. hydroxyl, amino, carboxy, etc. Moreover, according to the present invention, the solid-phase synthesis of the dienophile-modified oligonucleotides is conducted using an oxidizer, wherein iodine and $^{tert}$butylhydroperoxide are preferred, more preferably iodine is used as oxidizer for all synthesis cycles except for the last cycle when trans-cyclooctenol is coupled as dienophile and oxidized by $^{tert}$butylperoxide. After solid-phase synthesis, the oligonucleotides are cleaved from the solid support, purified via semi-preparative high-performance liquid chromatography (HPLC) and analysed by liquid chromatography-mass spectrometry (LC-MS; MS) or tandem liquid chromatography-mass spectrometry (LC-MSMS; MSMS).

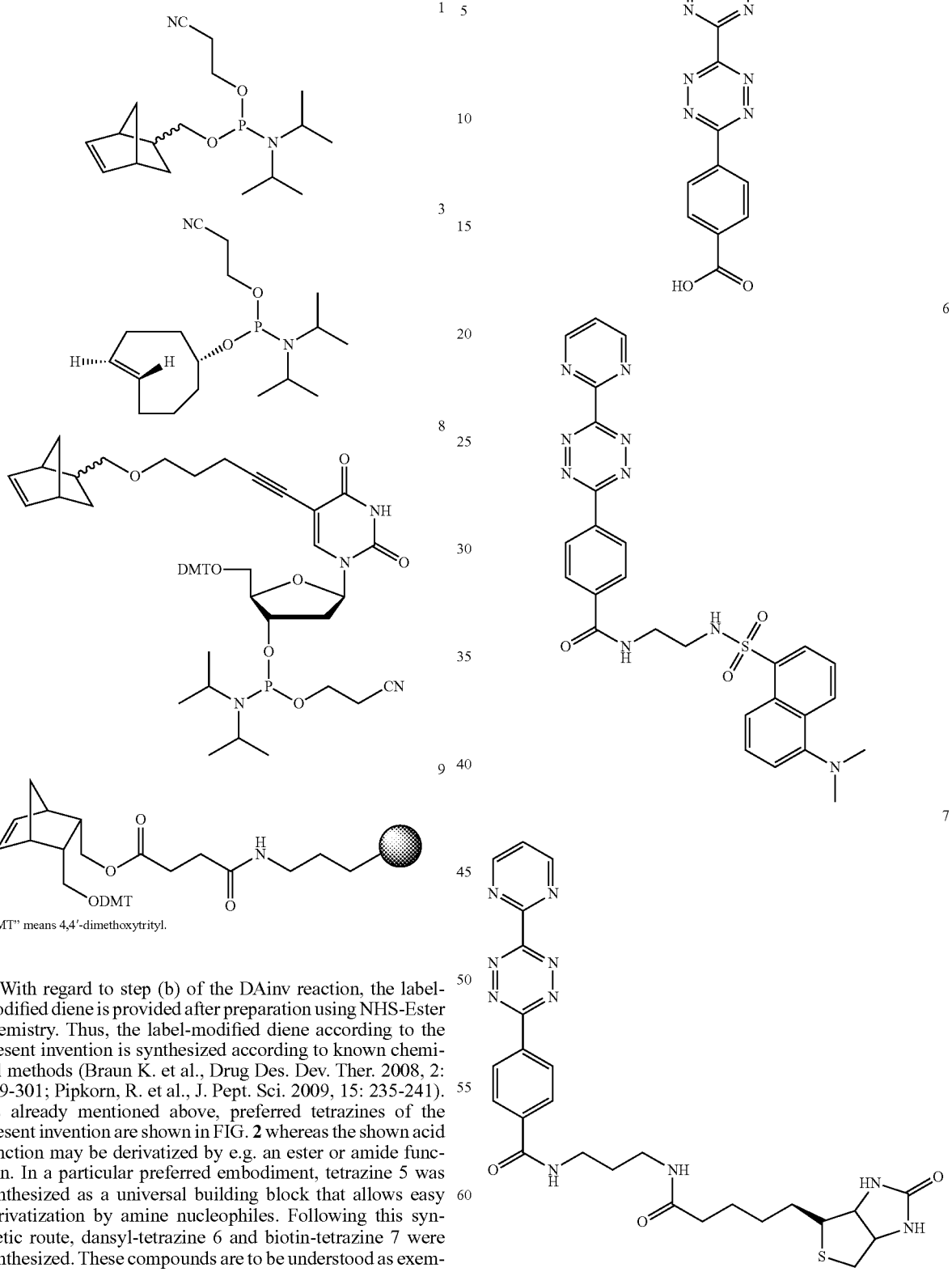

"DMT" means 4,4'-dimethoxytrityl.

With regard to step (b) of the DAinv reaction, the label-modified diene is provided after preparation using NHS-Ester chemistry. Thus, the label-modified diene according to the present invention is synthesized according to known chemical methods (Braun K. et al., Drug Des. Dev. Ther. 2008, 2: 289-301; Pipkorn, R. et al., J. Pept. Sci. 2009, 15: 235-241). As already mentioned above, preferred tetrazines of the present invention are shown in FIG. 2 whereas the shown acid function may be derivatized by e.g. an ester or amide function. In a particular preferred embodiment, tetrazine 5 was synthesized as a universal building block that allows easy derivatization by amine nucleophiles. Following this synthetic route, dansyl-tetrazine 6 and biotin-tetrazine 7 were synthesized. These compounds are to be understood as exemplary compounds carrying a label. For example any fluorescent, luminescent or phosphorescent dye or any other affinity tag may be bound to the tetrazine to allow labelling or tagging of the oligonucleotide after the following DAinv reaction.

Subsequent to the provision of the dienophile-modified oligonucleotide of step (a) and the label-modified diene of step (b), the electron-rich dienophile of step (a) reacts with the label-modified diene of step (b) via DAinv reaction, so that the electron-rich dienophile of the oligonucleotide is further converted by the DAinv reaction in which the label of choice can be attached.

The DAinv reaction of the method of the present invention between the dienophile-modified oligonucleotide and the label-modified diene uses preferably equimolar amounts of both components For oligonucleotide concentration below 10 µM labelling reactions, trans-cyclooctene is preferably used as dienophile. Using this dienophile, equimolar amounts of both components may be used for the labelling reaction even at low concentration and for oligonucleotides longer than 100 nucleotides.

In a further aspect of the DAinv reaction of the method of the present invention, yields of at least 60%, preferably at least about 80%, most preferred at least about 90% of DAinv reaction product can be obtained by the dienophile-modified oligonucleotides converted with the label-modified diene. In a preferred embodiment such yields of at least 60%, preferably at least about 80%, most preferred at least about 90% can be obtained by conversions applying equimolar amounts of the label-modified diene and the dienophile-modified oligonucleotide.

According to the method of the present invention, the other of the labelling reactions is the CuAAC reaction between an $N_3$-reactive group that is incorporated into an oligonucleotide via solid-phase synthesis and an $N_3$-modified label so that the $N_3$-reactive group of the oligonucleotide is further converted by the CuAAC reaction in which the label of choice can be attached.

In a preferable embodiment of the present invention, the CuAAC reaction is performed comprising steps (a')-(c') as procedural steps, which are consecutively performed (FIG. 3):
  (a') Providing of an oligonucleotide modified by the incorporation of one or more $N_3$-reactive groups, such as a terminal alkyne moiety, wherein the oligonucleotide may be modified either single or multiple and either terminally (3' or 5') or internally by solid-phase synthesis.
  (b') Providing of an $N_3$-modified label, i.e. of an azide that is modified with one or more labels.
  (c') Reaction of the $N_3$-reactive group(s) of step (a') with the $N_3$-modified label via CuAAC reaction.

Thus, the CuAAC reaction according to the present invention can be used to attach a $N_3$-modified label to an oligonucleotide containing one or more $N_3$-reactive groups. In detail, "azide" ($N_3$) as used in the present invention refers to an organic azide having a linear structure that may be drawn, according to the valence bond theory, as different resonating structures. Furthermore, the "$N_3$-reactive group" as used in the present invention refers to a terminal alkyne moiety that may be either an aliphatic or aromatic terminal alkyne moiety, preferably an aliphatic terminal alkyne moiety. Moreover, the "$N_3$-modified label" refers to a label containing a functional group that is modified with an azide, e.g. a biotin azide or a fluoropohore azide, such as Alexafluorazide or Cy5 azide.

With regard to step (a') of the CuAAC reaction, the modified oligonucleotide is provided after incorporating one or more $N_3$-reactive groups via solid-phase synthesis. With regard to step (b'), the $N_3$-modified label is provided after purchasing from Invitrogen (Life Technologies GmbH, Darmstadt, Germany). Subsequent to the provision of the modified oligonucleotide containing one or more $N_3$-reactive groups of step (a') and the $N_3$-modified label of step (b'), the $N_3$-reactive group of step (a') is conjugated with the $N_3$-modified label of step (b') by azide-alkyne-cycloaddition, i.e. the terminal alkyne moiety reacts with the azide employing the CuAAC reaction (copper-catalyzed click reaction).

With regard to the wording "copper-catalyzed click reaction", the "click-chemistry" is a term that was introduced by K. B. Sharpless in 2001 in order to describe reactions, i.e. "click reactions" that are usually bioorthogonal, high-yielding, and occur under relatively mild conditions (Best, M., Biochemistry, 2009, 48:6571-6584). They are wide in scope, create only byproducts that can be removed without chromatography, are stereospecific, simple to perform, and can be conducted in easily removable or benign solvents. This concept was developed in parallel with the interest within the pharmaceutical, materials, and other industries in capabilities for generating large libraries of compounds for screening in discovery research. Several types of reaction have been identified that fulfil these criteria, thermodynamically-favoured reactions that lead specifically to one product, such as nucleophilic ring opening reactions of epoxides and aziridines, non-aldol type carbonyl reactions, such as formation of hydrazones and heterocycles, additions to carbon-carbon multiple bonds, such oxidative formation of epoxides and Michael Additions, and cycloaddition reactions.

In detail, "copper-catalyzed click reaction" (Azide-Alkyne Huisgen Cycloaddition; CuAAC) generally means the copper-catalyzed 1,3-dipolar azide-alkyne-cycloaddition, i.e. a 1,3-dipolar cycloaddition between an azide and a terminal alkyne to give a 1,2,3-triazole such that in one preferable embodiment of the present invention the functionalization is accomplished via a copper-catalyzed 1,3-dipolar cycloaddition reaction between the incorporated $N_3$-modified nucleotide and a functional group containing a terminal alkyne moiety in the second step. Rolf Huisgen was the first to understand the scope of this organic reaction (Huisgen, R., Proc. Chem. Soc. London, 1961, 357). Here, the reactive groups needed (terminal alkynes and azides) are particularly small. Thus, they constitute only minor changes to the overall structure of nucleic acids modified with those groups, as well as the monomers needed to build up the oligonucleotides, so that enzymatic incorporation is more probable. As a result, a high number of different labels containing the matching reactive group can be incorporated in a subsequent chemical reaction. For example, the copper-catalyzed click reaction can be used to attach fluorophore azides to an enzymatically incorporated alkyne. However, instead of incorporating an alkyne into the oligonucleotide, it is also possible to incorporate an azide.

Furthermore, the CuAAC reaction of the present invention is preferably employed using a copper compound, i.e. copper (I) (Cu(I)) or a mixture of copper(II) (Cu(II)) with a "reducing agent" to produce Cu(I) in situ, wherein the use of Cu(II) with a reducing agent is preferred. The Cu(I) species of the present invention can be derived from commercial sources of Cu(I), which are selected from the group consisting of cuprous bromide or cuprous iodide. However, according to the present invention, Cu(II) species derived from Cu(II) sulphate ($CuSO_4$) are preferred.

Moreover, the CuAAC reaction of the present invention can be run in a variety of solvents and mixtures of water and a variety of partially miscible organic solvents including alcohols, dimethyl sulfoxide (DMSO), dimethylformamide (DMF), $^{tert}$butanol (tButOH) and acetone. As Cu(I) is unstable in aqueous solvents, stabilizing ligands are effective for improving the reaction outcome of the present invention, wherein tris-(benzyltriazolylmethyl)amine (TBTA) or tris-(3-hydroxypropyltriazolylmethyl)amine (THPTA) is preferably used, more preferably THPTA (FIG. 3).

Though the ligand does not have a direct influence on the integrity of the reaction product, the presence of a ligand has its advantages in the CuAAC reaction of the present invention. The ligand prevents the copper-ion from interacting with the oligonucleotide leading to degradation and formation of side products and also helps keeping the level of other harmful reaction products low. Furthermore, the ligand can potentially function as a proton acceptor thus eliminating the need of an additional base. Following, in a preferable embodiment of the present invention, the method of the present invention can be carried out in presence of a ligand and, thus, in absence of a base. This is advantageous, since the presence of an additional base can lead to increased oligonucleotide degradation.

Since the present invention provides a selective and simultaneous method for post-synthetic multiple orthogonal labelling of oligonucleotides, i.e. for at least dual orthogonal labelling of oligonucleotides, preferably RNA or DNA, the inverse Diels-Alder reaction (DAinv) and the copper-catalyzed click reaction (CuAAC) are simultaneously performed. Thus, this post-synthetic labelling of an oligonucleotide is based (i) on the DAinv reaction between one or more electron-rich dienophiles that are incorporated into an oligonucleotide and an electron-deficient diene that is modified with one or more labels and (ii) on the CuAAC reaction between one or more nucleotides containing one or more $N_3$-reactive groups that are also incorporated into the oligonucleotide and an $N_3$-modified label so that at least two labels of choice can be attached.

Figure 6:
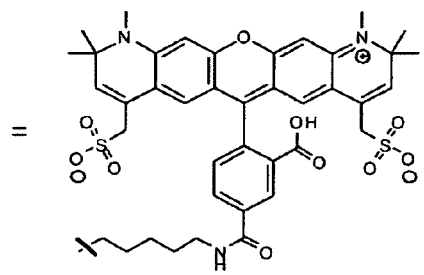
FIG. 6 shows the CuAAC reaction on a double-modified oligonucleotide.
Figure 6:
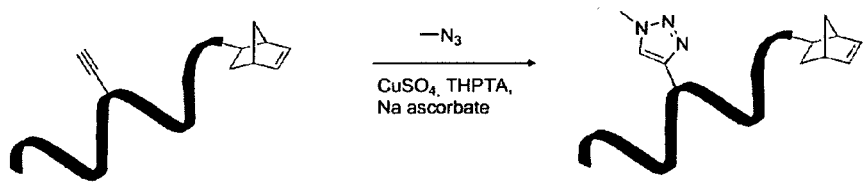

In a preferable embodiment, the method for multiple orthogonal labelling of the present invention comprises (FIG. 4, FIG. 5, FIG. 6):
- (a*) Providing of an oligonucleotide modified by the incorporation of one or more electron-rich dienophiles and one or more $N_3$-reactive groups, such as a terminal alkyne moiety, wherein the oligonucleotide may be modified either single or multiple and either terminally (3' or 5') or internally.
- (b*) Providing of a label-modified diene, i.e. of an electron-deficient diene that is modified with one or more labels.
- (c*) Providing of an $N_3$-modified label, i.e. of an azide that is modified with one or more labels.
- (d*) Reaction of the electron-rich dienophile(s) of step (a*) with the modified electron-deficient diene(s) via DAinv reaction.
- (e*) Reaction of the $N_3$-reactive group(s) of step (a*) with the $N_3$-modified label(s) via CuAAC reaction.

With regard to step (a*), that represent a combination of previous steps (a) and (a'), the multiple, or rather at least double-modified oligonucleotide is provided after incorporating one or more electron-rich dienophiles and one or more $N_3$-reactive groups, such as a terminal alkyne moiety, via solid-phase synthesis, wherein the solid-phase synthesis is carried out once for both type of modifications. With regard to steps (b*)-(e*) as listed above, the set of steps (b*) and (d*) refers to the DAinv reaction [see previous steps (b) and (c)] and the set of steps (c*) and (e*) refers to the CuAAC reaction [see previous step (b') and (c')], wherein the term "in a single step" means that the steps of DAinv reaction and the CuAAC reaction are simultaneously performed. This means, steps (a*)-(e*) of above do not represent steps that are consecutively performed but steps that are simultaneously performed in one pot, i.e. the set of steps (a*), (b*) and (d*) and the set of steps (a*), (c*) and (e*) are simultaneously performed. However, steps (a*), (b*), (d*) and steps (a*), (c*), (e*) are consecutively performed within the set, respectively.

Summarizing, the method is performed in a single step by adding the different reaction components together and incubating the reaction mixture, e.g. for one hour at room temperature, wherein the DAinv reaction takes place on the dienophile modification only and the CuAAC reaction selectively takes place on the $N_3$-reactive group modification, i.e. on the terminal alkyne. In detail, the present invention provides a one-pot multiple labelling method that allows the site-specific introduction of at least two different labels into oligonucleotides after solid-phase synthesis via simultaneously performing the DAinv and CuAAC reactions, wherein their particular features as described above may be also applied to this simultaneously performing of both labelling reactions.

Figure 7:
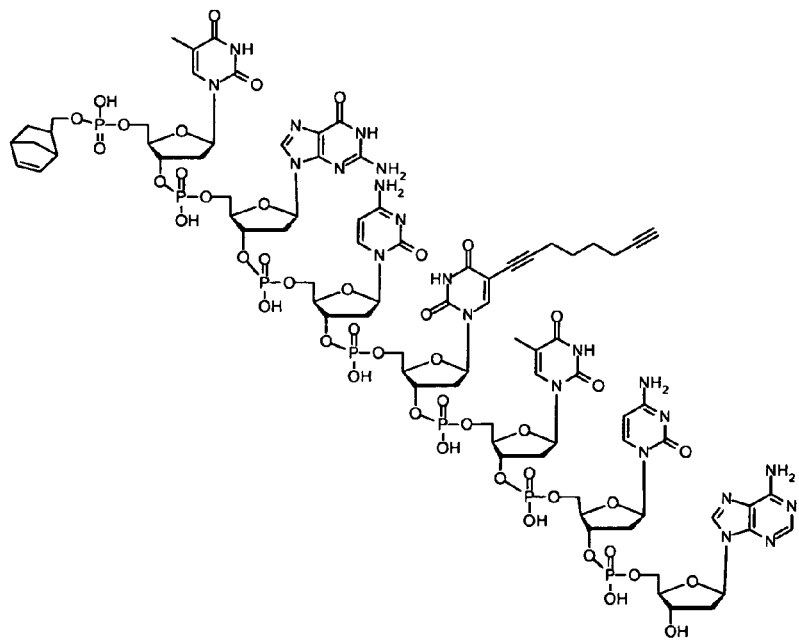
FIG. 7 shows a preferred double-modified oligonucleotide.
Figure 8:
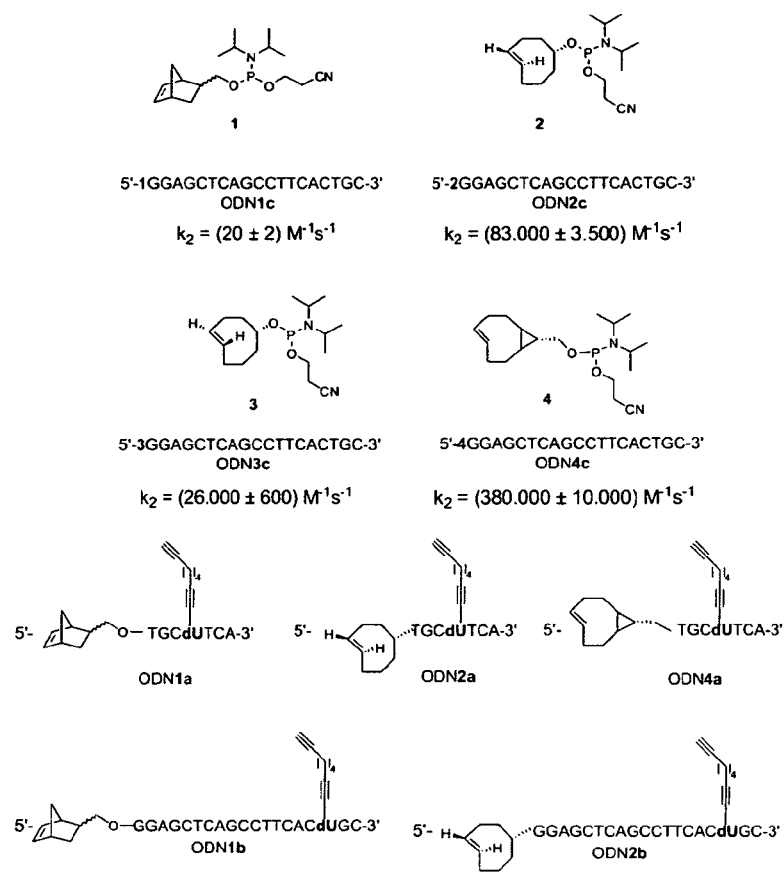
FIG. 8 shows dienophile-modified phosphoramidites 1-4 and synthesized oligonucleotides ODN1a-4c with corresponding rate constants of ODN1c-4c in the DAinv reaction.

In a preferred embodiment of the present invention, the "double-modified oligonucleotides" that are shown in FIG. 7 and FIG. 8 are produced by simultaneous incorporating one or more electron-rich dienophiles and one or more $N_3$-reactive groups via solid-phase synthesis. In a preferred embodiment of the present invention, the oligonucleotide is selected from the group consisting of ODN1a, ODN1b, ODN2a and ODN2b. Preferred building blocks for modifying oligonucleotides via click-chemistry is:

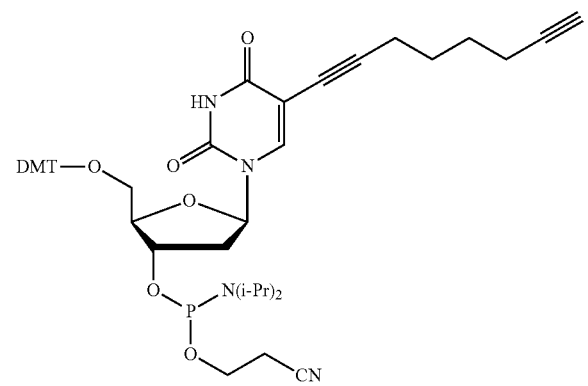

5-(Octa-1,7-diynyl)-3'-O-[(2-cyanoethoxy)(diisopropylamino)-phosphono)]-5'-O-(4, 4'-dimethoxytrityl)-2'-deoxyuridine These building blocks may be purchased from the Baseclick GmbH (Tutzing, Deutschland): (http://www.baseclick.eu/lproducts.php?search num str=BCA-03)

Thus, the term "multiple" of "multiple orthogonal labelling" as used in the present invention means that the oligonucleotides are labelled with more than one label, preferably with at least two labels. This could be achieved either by incorporating more than one electron-rich dienophile in step (a*) or by incorporating more than one nucleotide containing an $N_3$-reactive group in step (a*), or by modifying the electron-deficient diene of step (b*) with more than one label, or by modifying the azide of step (c*) with more than label, wherein any combination thereof is possible. In a preferred embodiment of the present invention, one electron-rich dienophile is incorporated in step (a*), one nucleotide containing one $N_3$-reactive group is incorporated in step (a*), the electron-deficient diene of step (b*) is modified with one label (single-modified diene), and the azide of step (c*) is modified with one label (single-modified azide), so that the one electron-rich dienophile of step (a*) reacts via DAinv reaction with the single-modified diene in step (d*), and the one nucleotide containing one $N_3$-reactive group of step (a*) reacts via CuAAC reaction with the single-modified azide in step (e*).

Preferably, during simultaneously performing the DAinv reaction and the CuAAC reaction for multiple orthogonal labelling of oligonucleotides of the present invention, the CuAAC reaction is performed with p-hydrochinone or sodium-ascorbate as reducing agent. Other possible reducing agents like Tris(carboxyethyl)phosphine (TCEP) may be chosen but sometimes undergo side reactions with the azide-moiety.

In another preferred embodiment of the present invention the method for post-synthetic multiple orthogonal labelling of oligonucleotides is employed between 5-50° C., preferably between 20-40° C., more preferably at 20, 25, 37 or 40° C., most preferably at room temperature (RT).

Furthermore, the reaction may take place in any suitable media having a pH<7, preferably in aqueous media. In a preferred embodiment, the reaction of the present invention may be run in a variety of solvents and mixtures of water and a variety of partially miscible organic solvents including alcohols, DMSO, DMF, $^{tert}$ButOH and acetone.

More specifically, the method for post-synthetic multiple orthogonal labelling of oligonucleotides according to the present invention may be performed at a pH-value ≤7, preferably between 4-7, more preferably between 4.5-5.5, even most preferably at 4.8. In a preferred embodiment of the present invention a buffer may be used in the reaction solution in order to maintain the pH-value, more preferably sodium acetate buffer (NaOAc).

According to the present invention, the reaction time of the method for multiple orthogonal labelling varies between 1 min and 18 h, wherein in a preferable embodiment the reaction time is 5-120 min, more preferably 5, 10, 20, 30, 60, 80 or 120 min, even more preferably 30, 60 or 120 min, most preferably 60 min.

Furthermore, the amount of the oligonucleotide to be labelled varies considerably depending on the experimental set up. While samples from natural sources can potentially be scarce, highly abundant natural oligonucleotides or chemically synthesized oligonucleotides are available at high concentrations. In a preferable embodiment of the method of this invention, the final oligonucleotide concentration varies depending on the reaction time and is adjusted between 0.05-500 μM, preferably between 0.2-80 μM, more preferably 0.2, 0.5, 4, 9, 10, 15, 20, 40 and 80 μM, even more preferably between 0.5-15 μM, most preferably 9 μM.

In summary, the present invention concerns a method for multiple orthogonal labelling of oligonucleotides, preferably RNA or DNA, by simultaneously performing the DAinv reaction and the CuAAC reaction, wherein the method is employed in a single step by just adding the different reaction components together and incubating the aqueous reaction mixture preferably for one hour at room temperature. In detail, the reaction components are one or more $N_3$-modified labels, a copper compound, a stabilizing ligand, a reducing agent and one or more electron-deficient label-modified dienes that are added together with an at least double-modified oligonucleotide having one more nucleotides containing one or more $N_3$-reactive groups and one or more electron-rich dienophiles, wherein a terminal alkyne moiety is preferably used as $N_3$-reactive group(s) and a trans-cyclooctene moiety or norbornene is preferably used as electron-rich dienophile(s), more preferably trans-cyclooctene. Therefore, the present invention provides a one-pot method for post-synthetic multiple orthogonal labeling of oligonucleotides, which allows the site-specific introduction of more than one label, preferably of at least two labels into oligonucleotides after solid-phase synthesis, wherein the DAinv takes place on the dienophile modification only and the CuAAC selectively takes place on the $N_3$-reactive group modification.

In a preferred embodiment, ODN1a is incubated for one hour at room temperature with dansyl-tetrazine for the DAinv reaction and with Alexafluorazide, CuSO$_4$, p-hydrochinone and THPTA for the CuAAC reaction in the respective concentration as described below (Table 1).

TABLE 1

Concentration scheme of the method for the multiple orthogonal labelling according to the present invention

| Reagent | | Final concentration |
|---|---|---|
| double-modified oligonucleotide having one or more nucleotides containing one or more $N_3$-reactive groups and one or more electron-rich dienophiles | preferably ODN1a, ODN1b, ODN2a, ODN2b | 0.5-15 μM, preferably 9 μM |
| buffer for pH 4-7 | preferably NaOAc buffer for preferably 4.8 | |
| $N_3$-modified label | preferably Alexafluorazide | 10-50 μM, preferably 36 μM |
| copper compound | preferably CuSO$_4$ | 500-1500 μM, preferably 900 μM |
| stabilizing ligand | preferably THPTA | 1-10 mM, preferably 4.5 mM |
| reducing agent | preferably sodium-ascorbate, p-hydrochinone | 5-25 mM, preferably 18 mM |
| electron-deficient label-modified diene | preferably dansyl-tetrazine | 5-50 μM, preferably 29 μM |

In addition, the present invention concerns a kit for the multiple orthogonal labelling of oligonucleotides, preferably RNA or DNA, by simultaneously performing the DAinv reaction and the CuAAC reaction, wherein the method of the kit is employed in a single step by just adding the different reaction components together and incubating the aqueous reaction mixture preferably for one hour at room temperature. In detail, the reaction components are one or more $N_3$-modified labels, a copper compound, a stabilizing ligand, a reducing agent and one or more electron-deficient label-modified dienes that are added together with an at least double-modified oligonucleotide having one or more nucleotides containing one or more $N_3$-reactive groups and one or more electron-rich dienophiles, wherein a terminal alkyne moiety is preferably used as $N_3$-reactive group(s) and a trans-cyclooctene moiety or norbornene is preferably used as electron-rich dienophile(s), more preferably trans-cyclooctene. Therefore, the present invention provides a kit that contains a one-pot method for post-synthetic multiple orthogonal labelling of oligonucleotides, which allows the site-specific introduction of more than one label, preferably of at least two labels into oligonucleotides after solid-phase synthesis, wherein the DAinv takes place on the dienophile modification only and the CuAAC selectively takes place on the $N_3$-reactive group modification.

In a preferred embodiment of the kit for the multiple orthogonal labelling of oligonucleotides, ODN1a is incubated for one hour at room temperature with dansyl-tetrazine for the DAinv reaction and with Alexafluorazide, CuSO$_4$, p-hydrochinone and THPTA for the CuAAC reaction in the concentration as described above (Table 1).

EXAMPLES

Hereinafter, the present invention is described in more detail and specifically with reference to the Examples, which however are not intended to limit the scope of the present invention.

In general, all reagents were purchased from Acros Organics (part of Thermo Fisher Scientific GmbH, Dreieich, Germany) or Sigma-Aldrich Chemie GmbH (Taufkirchen, Germany) and used without further purification. More specifically, the N$_3$-modified labels, such as Alexafluorazide, have been purchased from Invitrogen (Life Technologies GmbH, Darmstadt, Germany). The alkyne modifier were purchased as phosphoramidite from Baseclick GmbH (Tutzing, Germany).

Reversed-phase HPLC purification was performed on an Agilent 1100 Series HPLC system (Agilent Technologies, Waldbronn, Germany) equipped with a diode array detector using a semi-preparative Phenomenex Luna C18 5 µm column (15.0×250 mm; Phenomenex, Inc., Aschaffenburg, Gemany) using a flow rate of 5 ml/min and eluting with a gradient of 100 mM triethylammonium acetate pH 7.0 (buffer A) and 100 mM triethylammonium acetate in 80% acetonitrile (buffer B). HPLC-MS experiments were performed on a Bruker microTOFQ-II ESI mass spectrometer (Bruker Daltonik GmbH, Bremen, Germany) connected to an Agilent 1200 Series HPLC system equipped with a multi-wavelength detector. Therefore a Phemonenex kinetex C18 2.6 µm column (2.1×100 mm) was used and eluted at a flow rate of 0.2 ml/min using a gradient of 100 mM hexafluoroisopropanol/8.6 mM triethylamine pH 8.3 (LC-MS Buffer A) and methanol (LC-MS grade). Analysis of the LC-MS measurements was carried out using Hyphenation Star PP (Version 3.2.44.0) and Compass DataAnalysis (Version 4.0, SP 4) software (Bruker Daltonik GmbH, Bremen, Germany). Obtained MS-spectra were deconvoluted using Maximum Entropy deconvolution. For high-resolution, mass spectra internal calibration was performed (Enhanced quadratic mode) using ESI Tunemix (Fluka Analytical; part of Sigma-Aldrich Chemie GmbH, Taufkirchen, Germany) as calibrant. Calculated molecular weights refer to the m/z values given by the DataAnalysis software. NMR spectra were recorded on a Varian Mercury Plus 500 MHz spectrometer (Varian, Inc.; part of Agilent Technologies, Waldbronn, Germany). The assignment of proton and carbon resonances is based on two-dimensional correlation experiments (COSY, GHSQC, GHMBC). Oligonucleotide synthesis was performed on an Expedite™ 8909 automated synthesizer (Applied Biosystems) using standard reagents from Sigma Aldrich Proligo (Sigma-Aldrich Chemie GmbH, Taufkirchen, Germany).

Example 1

Synthesis of Phosphoramidites

The synthesis of 1 and 3 been performed according to PCT/EP2011/000491.

Synthesis of 2 and 4:

(E)-Cyclooct-4-enol (2a and 3a) (E)-cyclooct-4-enol was synthesized from (Z)-cyclooct-4-enol (Meier, H. et al., Chem. Ber. 1987, 120: 685-689) by modification of a previously described procedures (Royzen, M. et al., J. Am. Chem. Soc. 2008, 130: 3760-3761; Devaraj, N. K., et al., Angew. Chem. 2009, 48: 7013-7016). 2 g (15.9 mmol) (Z)-cyclooct-4-enol and 2.2 g (16.3 mmol) methyl benzoate were dissolved in 250 ml cyclohexane/diethyl ether=1:9. The Petri dish was placed in an UVP-CL-1000-ultraviolet crosslinker reactor and irradiated for eight hours under ice-cooling. In intervals of 25-30 minutes the reaction mixture was passed through a column packed with 27 g of silver nitrate-(10%) impregnated silica (commercially available from Aldrich). The mixture passing through the column was placed back into the UV crosslinker for further irradiation. After eight hours the irradiation was stopped and the silica was added to an ammonium hydroxide solution (160 ml, 28%). The suspension was stirred for 5 minutes, 160 ml of diethyl ether were added and stirring continued for 5 minutes. The aqueous layer was extracted with diethyl ether, the combined organic phases were washed with water and dried over magnesium sulfate. After evaporation of the solvents and flash chromatography (cyclohexane/ethyl acetate=1:1), two separated diastereomers of the product could be isolated. The major product as well as the minor product were obtained as colorless oils (minor, 2a: 280 mg, 2.22 mmol, 14%, major, 3a: 455 mg, 3.61 mmol, 23%).

The NMR data were in agreement with previously reported data (Royzen, M. et al., J. Am. Chem. Soc. 2008, 130: 3760-3761)

(E)-2-Cyanoethyl cyclooct-4-enyl diisopropylphosphoramidite (2). To a solution of minor trans-cyclooctenol (70 mg, 0.56 mmol) in 2 ml of anhydrous $CH_2Cl_2$ under argon, diisopropylethylamine (0.33 ml, 1.90 mmol) was added. The mixture was cooled to 0° C. and 2-cyanoethyl-N,N-diisopropyl-chlorophosphoramidite (141 µl, 0.63 mmol, 1.05 eq) was added. After stirring for one hour at RT, the reaction mixture was directly loaded on a silica column. Purification by flash chromatography (cyclohexane/ethyl acetate 4:1) yielded 2 as colorless oil (130 mg, 0.40 mmol, 71%).

$^1$H-NMR (500 MHz, CDCl$_3$, 25° C., TMS): δ=1.16-1.19 (m, 12H), 1.55-1.63 (m, 2H), 1.86-2.37 (m, 8H), 2.63 (t, J=6.55 Hz, 2H), 3.51-3.61 (m, 3H), 3.72-3.85 (m, 2H), 5.38-5.44 (m, 1H), 5.53-5.60 (m, 1H). $^{13}$C {$^1$H, $^{31}$P}NMR (125 MHz, CDCl$_3$, 25° C., TMS): δ=20.3, 24.4, 24.6, 31.1, 31.4, 32.7, 32.8, 34.4, 40.0, 40.3, 42.9, 43.0, 43.2, 58.1, 58.3, 79.6, 80.0, 117.6, 132.6, 135.1, 135.2. $^{31}$P-NMR (121 MHz, CDCl$_3$, 25° C., H$_3$PO$_4$): δ=145.5, 146.0 (mixture of 2 diastereomers). MS (APCI$^+$): m/z 327.21 (calculated for [C$_{17}$H$_{31}$N$_2$O$_2$P$_1$+H]+327.21)

(E)-2-Cyanoethyl cyclooct-4-enyl diisopropylphosphoramidite (3). The same procedure as for synthesis of 2 was used, starting from major trans-cyclooctenol. The product was obtained as colorless oil (100 mg, 0.31 mmol, 55%).

$^1$H-NMR (500 MHz, CDCl$_3$, 25° C., TMS): δ=1.19-1.24 (m, 12H), 1.57-1.64 (m, 1H), 1.72-2.34 (m, 8H), 2.32-2.46 (m, 1H), 2.60-2.64 (m, 2H), 3.61-3.70 (m, 2H), 3.71-3.80 (m, 1H), 3.79-3.82 (m, 1H), 4.10-4.18 (m, 1H), 5.46-5.53 (m, 1H), 5.58-5.66 (m, 1H). $^{13}$C {$^1$H, $^{31}$P}NMR (125 MHz, CDCl$_3$, 25° C., TMS): δ=20.5, 24.5, 24.6, 24.7, 28.1, 28.5, 29.7, 30.1, 34.1, 34.4, 34.5, 42.9, 43.0, 43.1, 57.8, 57.9, 70.0, 70.3, 117.6, 117.7, 131.5, 131.7, 135.5, 135.8. $^{31}$P-NMR (121 MHz, CDCl$_3$, 25° C., H$_3$PO$_4$): δ=145.9, 146.2 (mixture of 2 diastereomers). MS (HR-APCI$^+$) m/z 327.2196 (calculated for [C$_{17}$H$_{31}$N$_2$O$_2$P$_1$+H]$^+$ 327.2196).

In addition a further trans-Cyclooctenol-Dienophile has been synthesized, exhibiting a higher reactivity in DARinv than trans-Cyclooctenol 2 and 3:

endo-(E)-bicyclo[6.1.0]non-4-en-9-ylmethanol (4a). endo-(E)-bicyclo[6.1.0]non-4-en-9-ylmethanol was synthesized by modification of a previously published procedure (Taylor, M. T.; Blackman, M. L.; Dmitrenko, O.; Fox, J. M., J. Am. Chem. Soc. 2011, 133, 9646-9). 950 mg (6.24 mmol) (Z)-bicyclo[6.1.0]non-4-en-9-ylmethanol and 1.7 g (12.6 mmol) methyl benzoate were dissolved in 300 ml cyclohexane/diethyl ether=1:1. The Petri dish was placed in an UVP-CL-1000-ultraviolet crosslinker reactor and irradiated for eight hours under ice-cooling. In intervals of 20 minutes the reaction mixture was passed through a column packed with 10.7 g of silver nitrate-(10%) impregnated silica (commercially available from Aldrich). The mixture passing through the column was placed back into the UV crosslinker for further irradiation. After eight hours the irradiation was stopped and the silica was added to an ammonium hydroxide solution (200 ml, 28%). The suspension was stirred for 5 minutes, 200 ml of diethyl ether were added and stirring continued for 10 minutes. The aqueous layer was extracted with ether, the combined organic phases were washed with water, dried over sodium sulfate and solvents evaporated. Purification by flash chromatography (cyclohexane/ethyl acetate=4:1) yielded the product (633 mg, 4.16 mmol, 67%) as colorless oil.

The NMR data were in agreement with previously reported data (Taylor, M. T.; Blackman, M. L.; Dmitrenko, O.; Fox, J. M., J. Am. Chem. Soc. 2011, 133 (25) 9646-9).

endo-(E)-2-Cyanoethyl bicyclo[6.1.0]non-4-en-9-methyl diisopropylphosphoramidite (4). To a solution of endo-(E)-bicyclo[6.1.0]non-4-en-9-ylmethanol (69 mg, 0.45 mmol) in 1.5 ml of anhydrous $CH_2Cl_2$ under argon, diisopropylethylamine (0.25 ml, 1.44 mmol) was added. The mixture was cooled to 0° C. and 2-cyanoethyl-N,N-diisopropylchlorophosphoramidite (106 µl, 0.48 mmol, 1.05 eq) was added. After stirring for one hour at RT, the reaction mixture was directly loaded on a silica column. Purification by flash chromatography (cyclohexane/ethyl acetate 4:1) yielded the product as colorless oil (138 mg, 0.39 mmol, 87%).

$^1$H-NMR (500 MHz, $CDCl_3$, 25° C., TMS): δ=0.35-0.61 (m, 4H), 0.85 (ddd, J=23.97, 12.24, 6.80 Hz, 1H), 1.17 (2d, J=6.91 Hz, 12H), 1.84-1.98 (m, 2H), 2.16-2.41 (m, 4H), 2.64 (t, J=6.57 Hz, 2H), 3.51-3.66 (m, 4H), 3.76-3.87 (m, 2H), 5.08-5.18 (m, 1H), 5.82-5.93 (m, 1H). $^{13}$C {$^1$H}NMR (75 MHz, $CDCl_3$, 25° C., TMS): δ=20.3, 20.4, 20.8, 20.9, 21.9, 22.0, 24.5, 24.6, 26.8, 27.7, 32.7, 33.9, 38.7, 42.9, 43.1, 58.1, 58.4, 68.0, 68.1, 117.6, 131.2, 138.4). $^{31}$P-NMR (121 MHz, $CDCl_3$, 25° C., $H_3PO_4$): δ=147.7 (mixture of 2 diastereomers). MS (HR-APCII) m/z 353.2363 (calculated for $[C_{19}H_{33}N_2O_2P_1+H]$+353.2352).

Example 2

Figure 9:
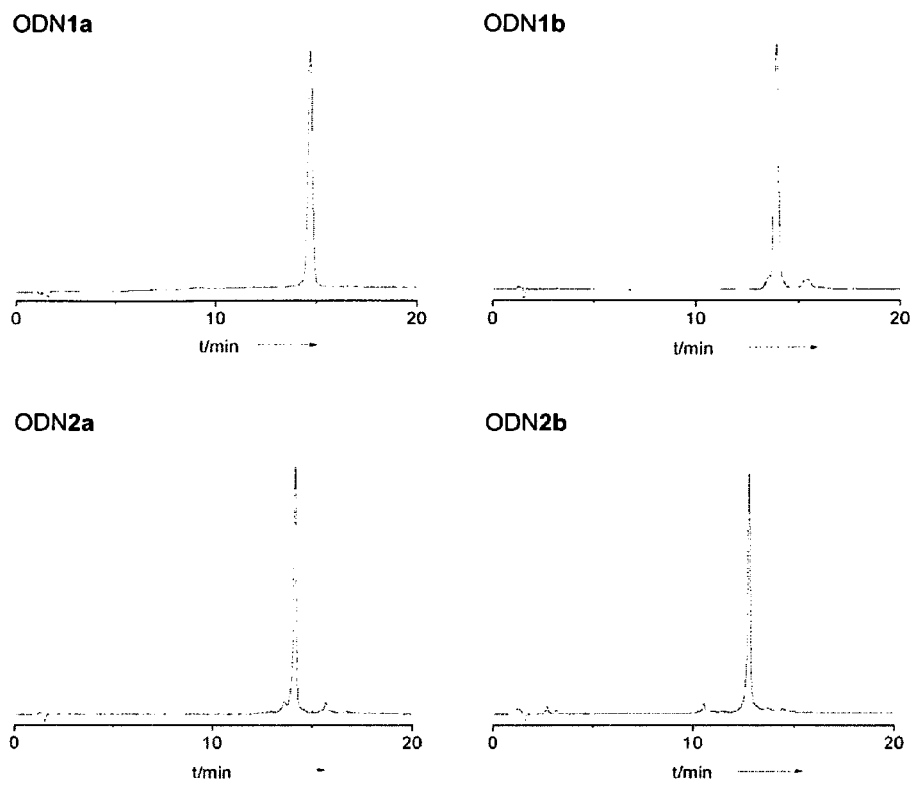
FIG. 9 shows the HPLC-chromatograms of the double-modified oligonucleotides ODN1a, ODN2a, ODN1b, ODN2b.
Figure 10:
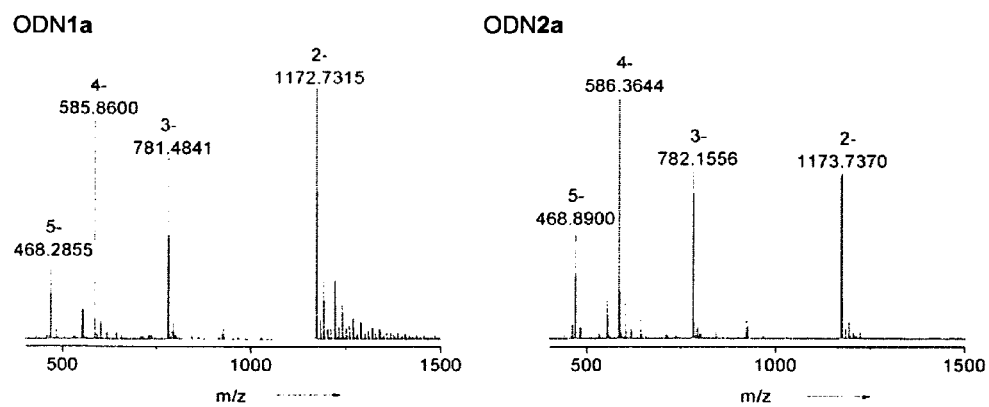

Synthesis of the Double-modified Oligonucleotides ODN1a, ODN1b, ODN2a, ODN2b and their HPLC, LC-MS and/or LC-MSMS Analysis Oligonucleotide synthesis was performed on an Expedite™ 8909 automated synthesizer in 1 µmolar scale. By using standard reagents, the incorporation of trans-cyclooctene phosphoramidite failed. In further investigations it turned out that trans-cyclooctene is unstable against the standard oxidizer Iodine and is therefore getting destroyed during the oxidizing cycle of the synthesis. By substituting Iodine against $^{tert}$Butylhydroperoxide (1 M in dichloromethane, DCM) the trans-cyclooctene modification was still intact after the oxidation. Solid phase synthesis was finally conducted using Iodine as oxidizer for all synthesis cycles except the last cycle where trans-cyclooctene was coupled and oxidized by $^{tert}$Butylperoxide. After synthesis, oligonucleotides ODN1a, ODN1b, ODN2a, ODN2b were cleaved from the solid support (controlled pore glass, CPG) and purified via semi-preparative HPLC and analysed via LC-MS and/or LC-MSMS The gradient used for semi-preparative HPLC purification was an increase from 10% buffer B to 35% buffer B over 25 min. The gradient used for LC-MS analysis was an increase from 15% methanol to 35% methanol over 20 min. The LC-chromatograms (LC-MS) or rather the retention times of ODN1a, ODN1b, ODN2a, and ODN2b obtained are shown in Table 2 and FIG. 9, wherein ODN1a and ODN1b represent shorter oligonucleotides and ODN2a and ODN2b represent longer oligonucleotides. MS spectra of ODN1a and ODN2a are shown in FIG. 10, wherein the LC-MS results, i.e. [M] calculated and [M] deconvoluted are shown in Table 2.

TABLE 2

LC-MS, HPLC and HR-ESI analysis of the synthesized oligonucleotides

| ODN | retention time [min] | [M] calculated | [M] deconvoluted | deviation [ppm] |
|---|---|---|---|---|
| ODN1a | 14.8 | 2346.4762 | 2346.4846 | 3.6 |
| ODN1b | 13.9 | 6040.0853 | 6040.1039 | 3.1 |
| ODN2a | 14.1 | 2349.4956 | 2349.5042 | 3.7 |
| ODN2b | 12.8 | 6042.1010 | 6042.0973 | 0.6 |

Figure 11:
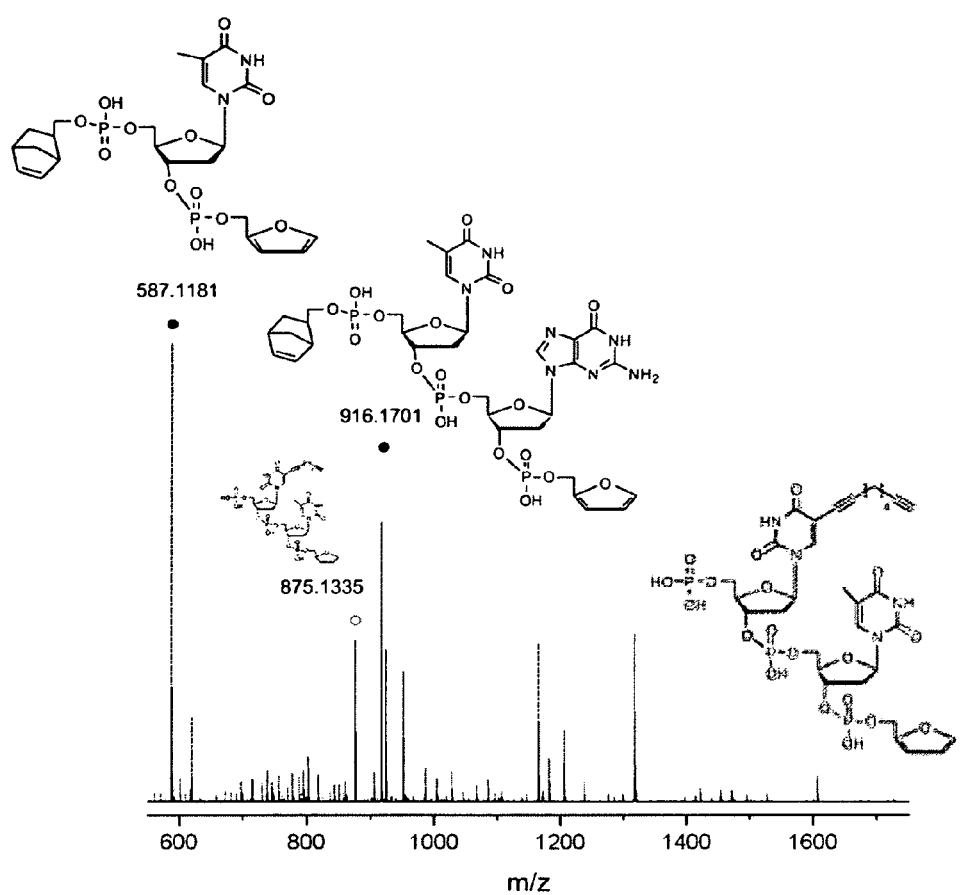
Figure 12:
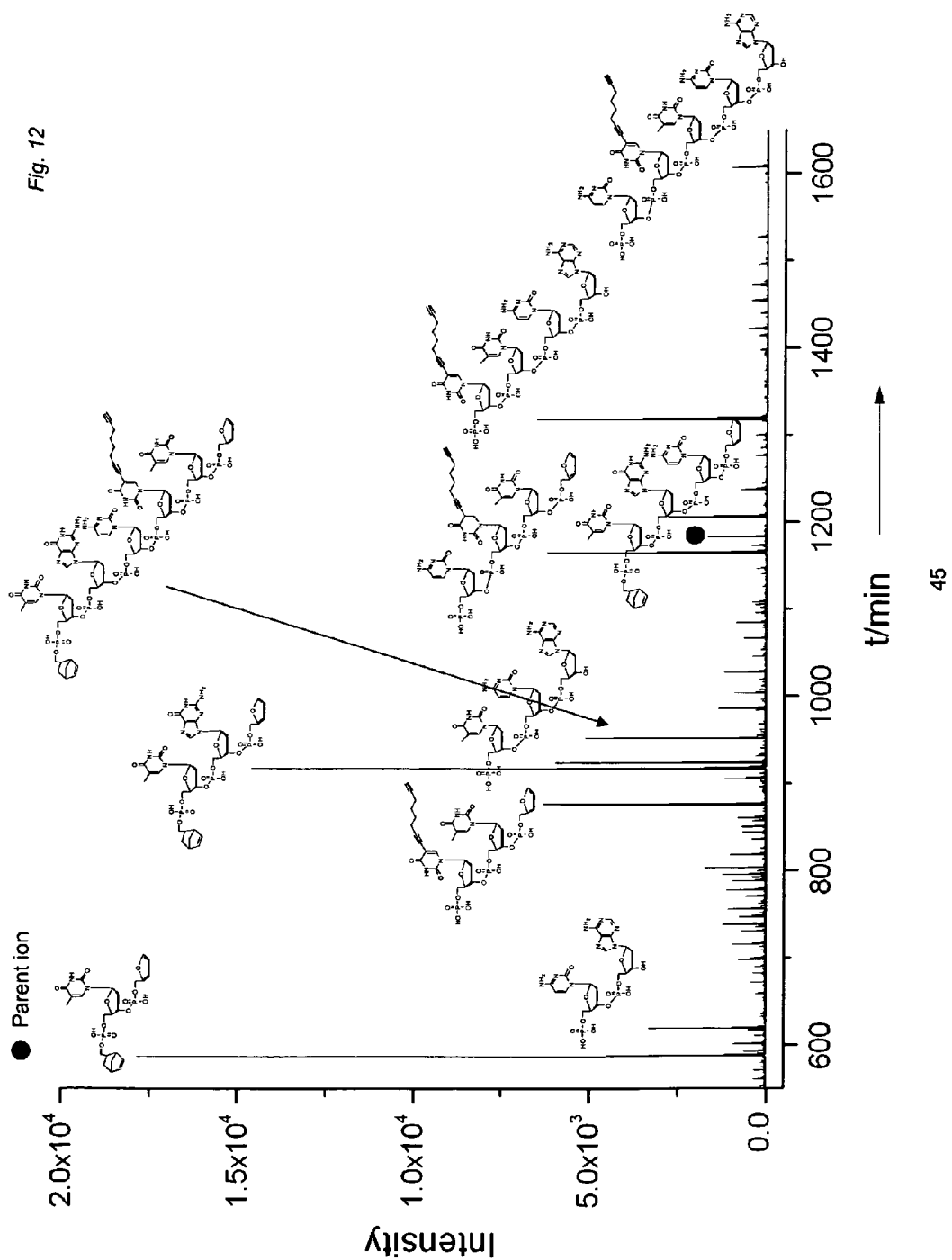

For the MSMS-measurements, double-charged peak at 1172 (ODN1a) and 1173 (ODN2a), respectively, were taken as parent ion, wherein the settings for the MSMS-measurements were the following: ODN1a (isolation ion: 1172; isolation width: 10; collision energy: 40 eV; acquisition factor: 100) and ODN2a (isolation ion: 1173; isolation width: 10; collision energy: 40 eV; acquisition factor: 100). As the same fragmentation scheme was obtained for ODN1a and ODN2a, only MSMS-spectrum and fragmentation pattern of ODN1a is described in detail (FIG. 11 and FIG. 12).

A summary of the MSMS analysis of ODN1a is shown in Table 3.

TABLE 3

Results of the MSMS analysis of ODN1a

| Fragment | Molecular formula | m/z calculated | m/z obtained |
|---|---|---|---|
| 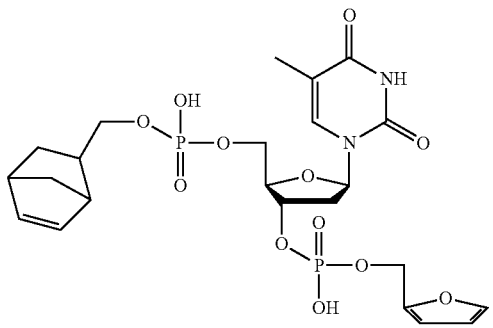 | $[C_{23}H_{30}N_2O_{12}P_2—H]^-$ | 587.1201 | 587.1181 |

TABLE 3-continued

Results of the MSMS analysis of ODN1a

| Fragment | Molecular formula | m/z calculated | m/z obtained |
|---|---|---|---|
| | [C$_{19}$H$_{26}$N$_8$O$_{12}$P$_2$—H]$^-$ | 619.1073 | 619.1072 |
| | [C$_{32}$H$_{39}$N$_4$O$_{19}$P$_3$—H]$^-$ | 875.1349 | 875.1335 |
| | [C$_{33}$H$_{42}$N$_7$O$_{18}$P$_3$—H]$^-$ | 916.1726 | 916.1701 |

TABLE 3-continued
Results of the MSMS analysis of ODN1a
| Fragment | Molecular formula | m/z calculated | m/z obtained |
| --- | --- | --- | --- |
| 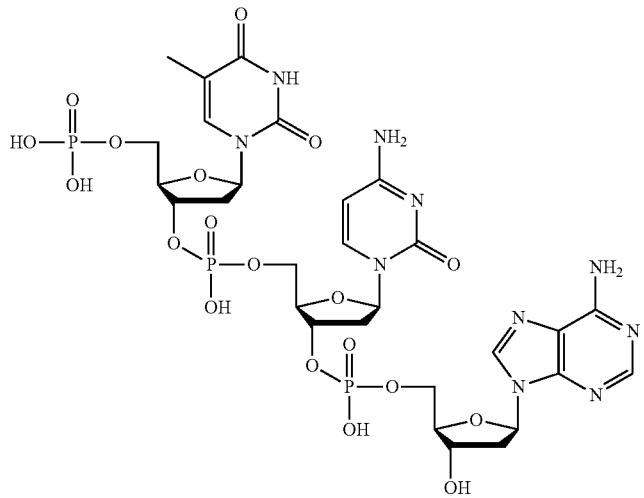 | C$_{29}$H$_{39}$N$_{10}$O$_{19}$P$_3$—H]$^-$ | 923.1533 | 923.1502 |
| 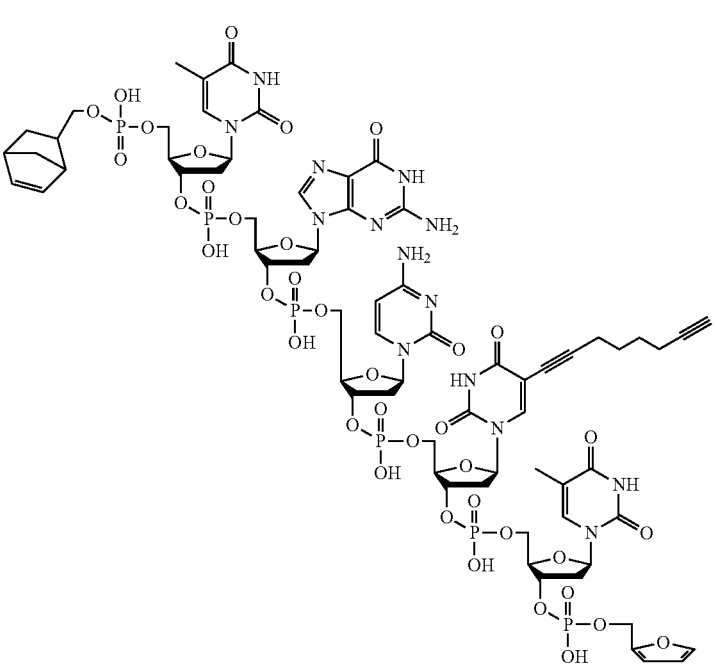 | [C$_{69}$H$_{86}$N$_{14}$O$_{38}$P$_6$—2H]$^{-2}$ | 951.1754 | 951.1750 |

TABLE 3-continued

Results of the MSMS analysis of ODN1a

| Fragment | Molecular formula | m/z calculated | m/z obtained |
|---|---|---|---|
| (structure) | $[C_{41}H_{51}N_7O_{25}P_4-H]^-$ | 1164.1812 | 1164.1761 |
| (structure) | $[C_{42}H_{54}N_{10}O_{24}P_4-H]^-$ | 1205.2190 | 1205.2142 |

TABLE 3-continued

Results of the MSMS analysis of ODN1a

| Fragment | Molecular formula | m/z calculated | m/z obtained |
|---|---|---|---|
| 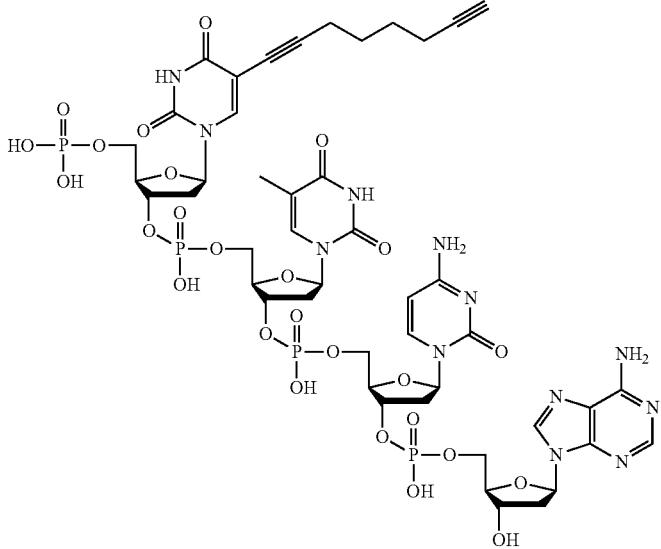 | [$C_{46}H_{58}N_{12}O_{26}P_4$—H]$^-$ | 1317.2463 | 1317.2392 |
| 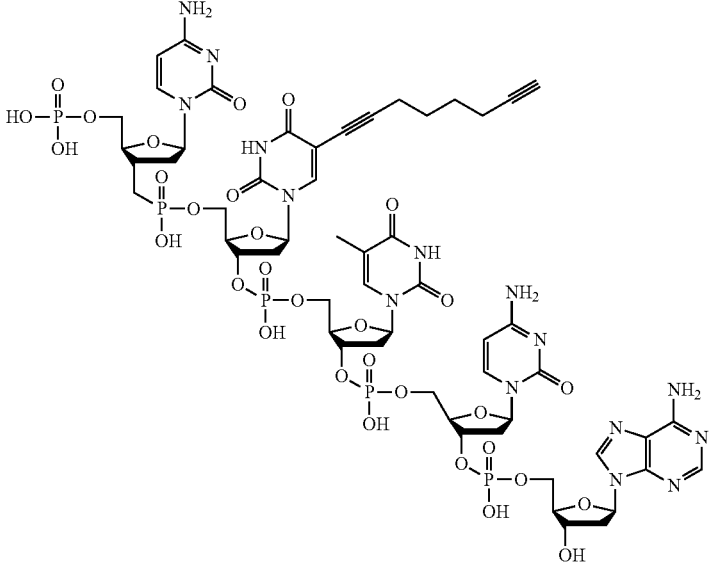 | [$C_{55}H_{70}N_{15}O_{32}P_5$—H]$^-$ | 1606.2927 | 1606.2838 |

Example 3

HPLC, LC-MS and/or LC-MSMS Analysis of the DAinv Reaction Product

For DAinv reaction, stock solutions of the oligonucleotides ODN1a, ODN1b, ODN2a, ODN2b and dansyl-tetrazine were mixed at 1:1 stoichiometry in a final concentration of 63 µM. After incubation at room temperature (RT) for one hour, 45 µl of water were added and the reaction mixture was directly injected into the LC-MS.

The retention times of the DAinv ODN1a, DAinv ODN1b, DAinv ODN2a, and DAinv ODN2b reaction products are shown in Table 4.

TABLE 4

LC-MS, HPLC and HR-ESI analysis of the DAinv ODN1a, DAinv ODN1b, DAinv ODN2a, and DAinv ODN2b reaction products

| ODN | retention time [min] | [M] calculated | [M] deconvoluted | deviation [ppm] |
|---|---|---|---|---|
| ODN1a | 17.4-22.5 | 2874.6536 | 2874.6704 | 5.8 |
| ODN1b | 12.7-15.6 | 6568.2630 | 6568.2786 | 2.4 |
| ODN2a | 15.9-20.4 | 2876.6687 | 2876.6815 | 4.5 |
| ODN2b | 9.7-11.8 | 6570.2786 | 6570.2738 | 0.7 |

Figure 13:
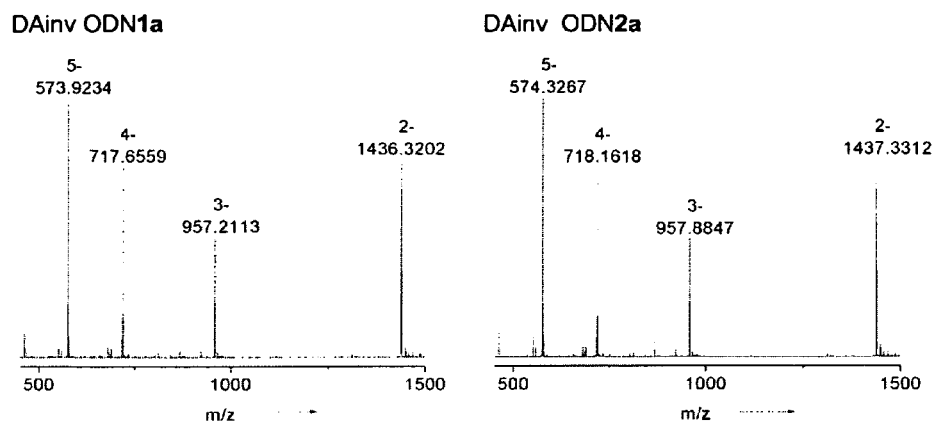
FIG. 13 shows the MS spectra of the double-modified oligonucleotides DAinv ODN1a and ODN2a reaction products.

The gradient used for LC-MS analysis was an increase from 20% methanol to 50% methanol over 30 min. MS spectra of the DAinv ODN1a and DAinv ODN2a reaction products are shown in FIG. 13, wherein the MS results, i.e. [M] calculated and [M] deconvoluted are shown in Table 4.

Figure 14:
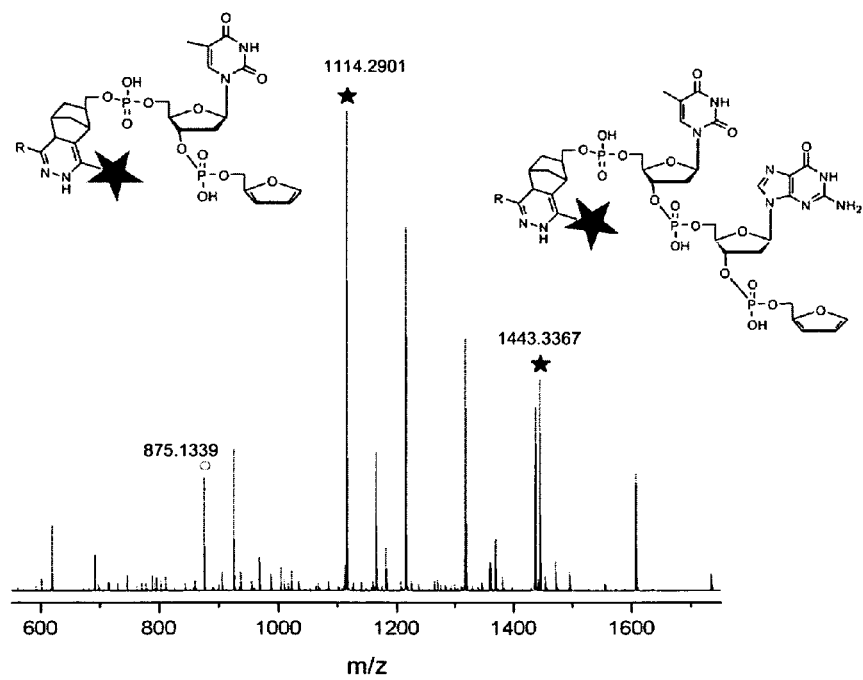
FIG. 14 shows the MSMS spectrum for the double-modified ODN1a DAinv reaction product.
Figure 15:
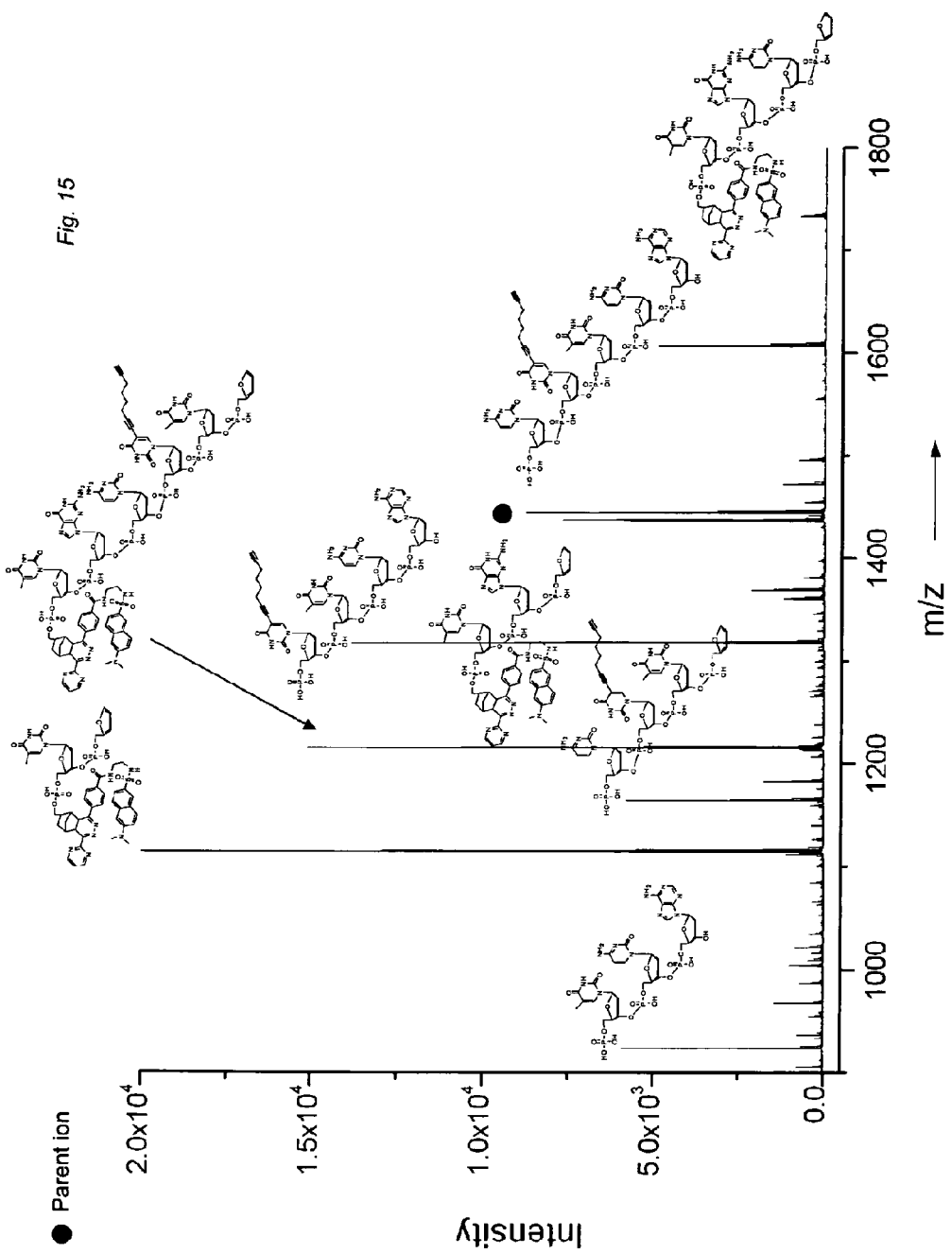
FIG. 15 shows the detailed MSMS spectrum for the double-modified ODN1a DAinv reaction product.

For the MSMS-measurements, double-charged peak at 1436 (DAinv ODN1a) and 1437 (DAinv ODN2a), respectively, were taken as parent ion, wherein the settings for the MSMS-measurements were the following: DAinv ODN1a (isolation ion: 1436; isolation width: 10; collision energy: 40 eV; acquisition factor: 100) and DAinv ODN2a (isolation ion: 1437; isolation width: 10; collision energy: 40 eV; acquisition factor: 100). As the same fragmentation scheme was obtained for DAinv ODN1a and DAinv ODN2a reaction products, only MSMS-spectrum and fragmentation pattern of DAinv ODN1a reaction product is described in detail (FIG. 14 and FIG. 15).

A summary of the MSMS analysis of the DAinv ODN1a reaction product is shown in Table 5.

TABLE 5

Results of the MSMS analysis of the DAinv ODN1a reaction product

| Fragment | Molecular formula | m/z calculated | m/z measured |
|---|---|---|---|
| 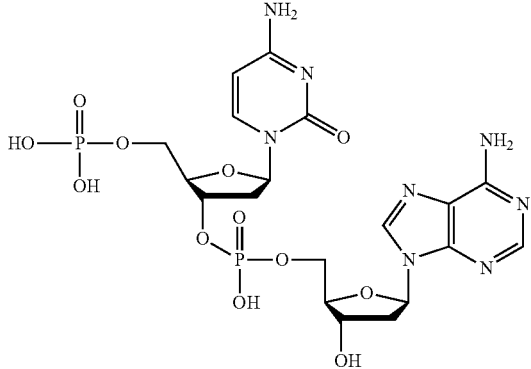 | $[C_{19}H_{26}N_8O_{12}P_2-H]^-$ | 619.1073 | 619.1053 |
| 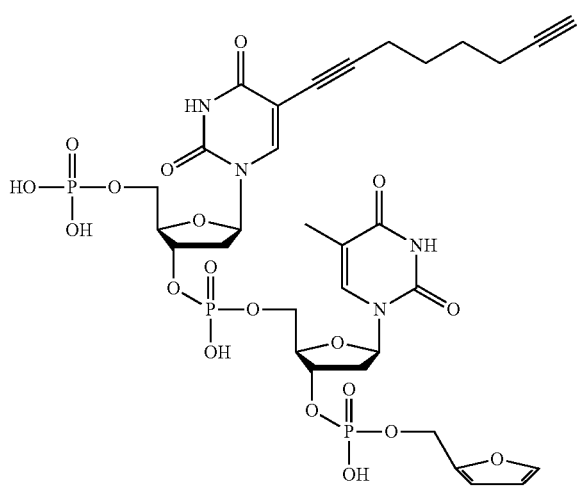 | $[C_{32}H_{39}N_4O_{19}P_3-H]^-$ | 875.1349 | 875.1339 |

TABLE 5-continued

Results of the MSMS analysis of the DAinv ODN1a reaction product

| Fragment | Molecular formula | m/z calculated | m/z measured |
|---|---|---|---|
| (structure) | $[C_{29}H_{39}N_{10}O_{19}P_3-H]^-$ | 923.1533 | 923.1520 |
| (structure) | $[C_{50}H_{55}N_9O_{15}P_2S-H]^-$ | 1114.2941 | 1114.2901 |
| (structure) | $[C_{41}H_{51}N_7O_{25}P_4-H]^-$ | 1164.1812 | 1164.1758 |

TABLE 5-continued
Results of the MSMS analysis of the DAinv ODN1a reaction product
| Fragment | Molecular formula | m/z calculated | m/z measured |
|---|---|---|---|
| 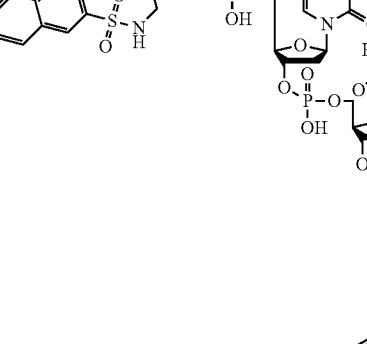 | [C₉₆H₁₁₁N₂₁O₄₁P₆S—2H]⁻² | 1214.7624 | 1214.7562 |
| 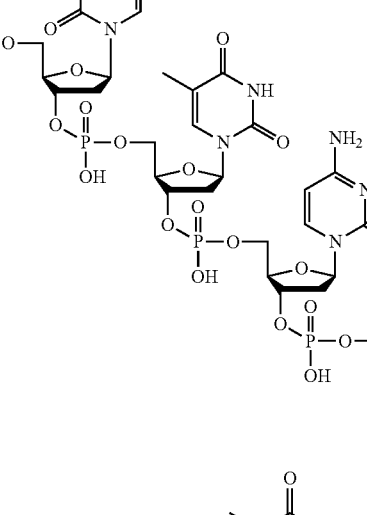 | [C₄₆H₅₈N₁₂O₂₆P₄—H]⁻ | 1317.2463 | 1317.2380 |
| 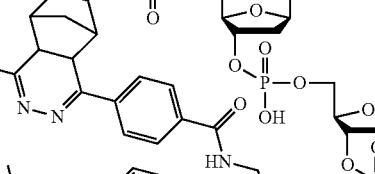 | [C₆₀H₆₇N₁₄O₂₁P₃S—H]⁻ | 1443.3466 | 1443.3367 |

TABLE 5-continued

Results of the MSMS analysis of the DAinv ODN1a reaction product

| Fragment | Molecular formula | m/z calculated | m/z measured |
|---|---|---|---|
| 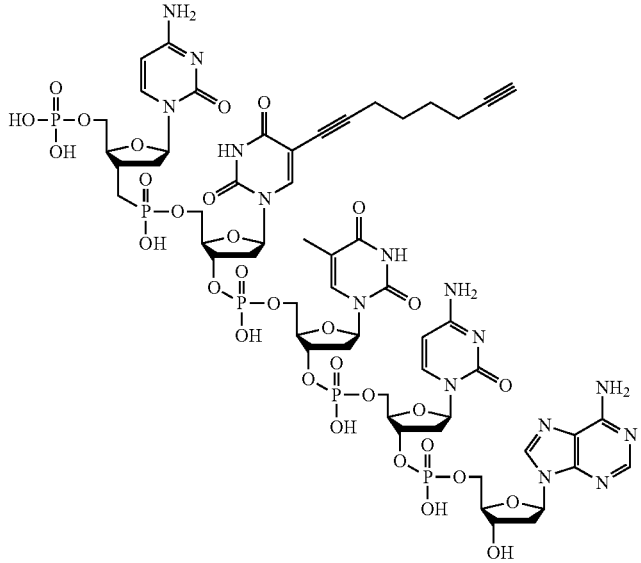 | [C$_{55}$H$_{70}$N$_{15}$O$_{32}$P$_5$—H]$^-$ | 1606.2927 | 1606.2816 |
| 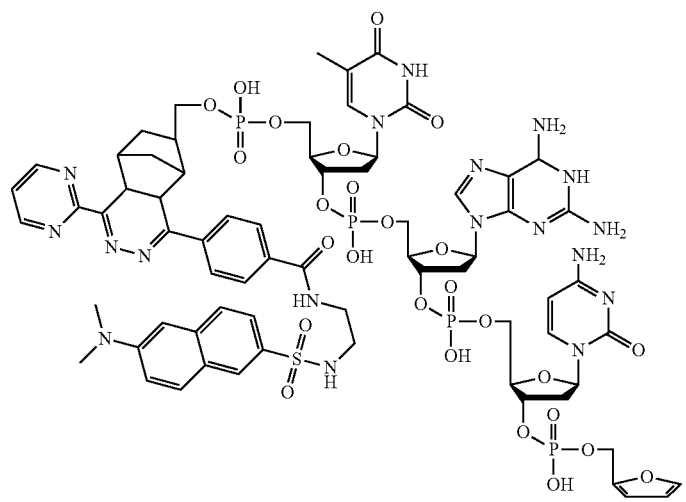 | [C$_{69}$H$_{79}$N$_{17}$O$_{27}$P$_4$S—H]$^-$ | 1732.3930 | 1732.3789 |

Example 4

HPLC, LC-MS and/or LC-MSMS Analysis of the CuAAC Reaction Product

For the analysis of the CuAAC reaction products, the following pipetting scheme was used as shown in Table 6.

TABLE 6

Pipetting scheme for performing CuAAC reaction

| | | Stock concentration | Final concentration |
|---|---|---|---|
| 3.1 µl | Oligonucleotide | 80 µM | 9 µM |
| 19.7 µl | NaOAc buffer pH 4.79 | | |
| 1 µl | Alexafluorazide | 1 mM in DMSO | 36 µM |
| 0.5 µl | CuSO$_4$ | 50 mM | 900 µM |
| 2.5 µl | THPTA | 50 mM | 4.5 mM |
| 1 µl | Na-ascorbate | 500 mM | 18 mM |

Stock solutions were combined in the above order, whereas CuSO$_4$ and THPTA were mixed before addition to the reaction mixture. After incubating for one hour at room temperature the samples were diluted to 55 µl and injected into LC-MS. In case of the longer oligonucleotides ODN1b and ODN2b, oligonucleotides were isopropanol precipitated before subjecting to LC-MS analysis.

The retention times of the CuAAC ODN1a, CuAAC ODN2a, CuAAC ODN1b, and CuAAC ODN2b reaction products are shown in Table 7.

TABLE 7

LC-MS, HPLC and HR-ESI analysis of the CuAAC ODN1a, CuAAC ODN1b, CuAAC ODN2a, and CuAAC ODN2b reaction products

| ODN | Retention time [min] | [M] calculated | [M] deconvoluted | Deviation [ppm] |
|---|---|---|---|---|
| ODN1a | 18.5-19.5 | 3193.7508 | 3193.7565 | 1.8 |
| ODN1b | 12.5-13.1 | 6887.3355 | 6887.3299 | 0.8 |
| ODN2a | 16.4-17.4 | 3195.7665 | 3195.7774 | 3.4 |
| ODN2b | 13.2-13.9 | 6889.3512 | 6889.3549 | 0.5 |

Figure 16:
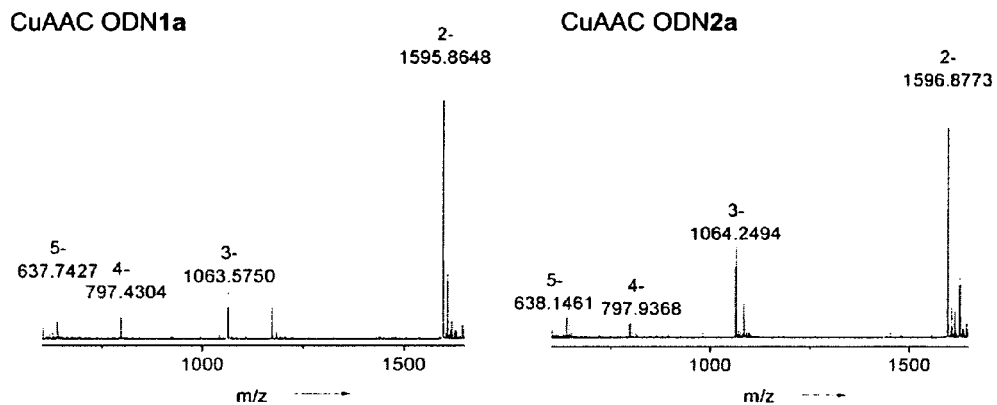
FIG. 16 shows the MS spectra of the double-modified CuAAC ODN1a and CuAAC ODN2a reaction products.

The gradient used for LC-MS analysis was an increase from 20% methanol to 50% methanol over 30 min. MS spectra of the DAinv ODN1a and DAinv ODN2a reaction products are shown in FIG. 16, wherein the MS results, i.e. [M] calculated and [M] deconvoluted are shown in Table 7.

Figure 17:
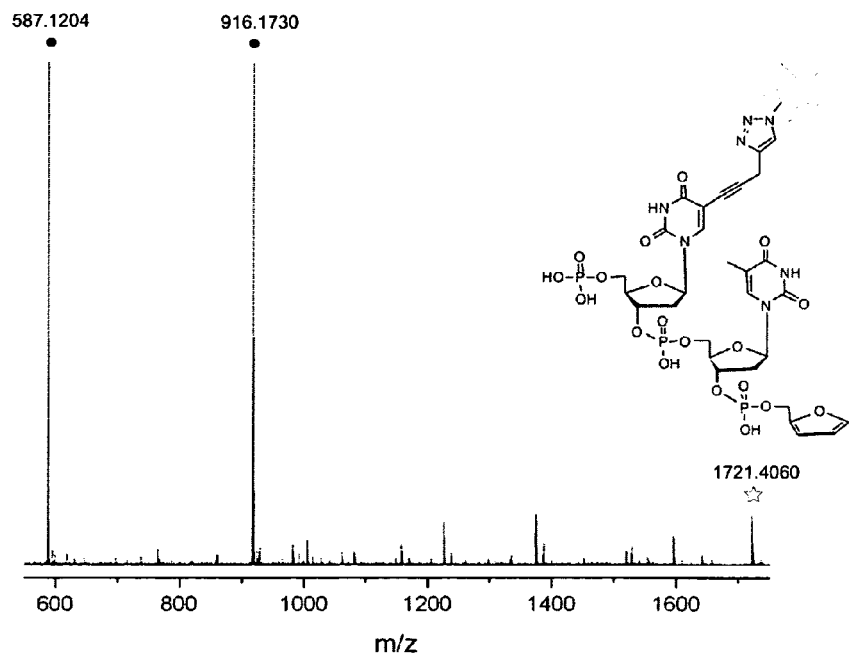
FIG. 17 shows the MSMS spectrum for the double-modified CuAAC ODN1a reaction product.
Figure 18:
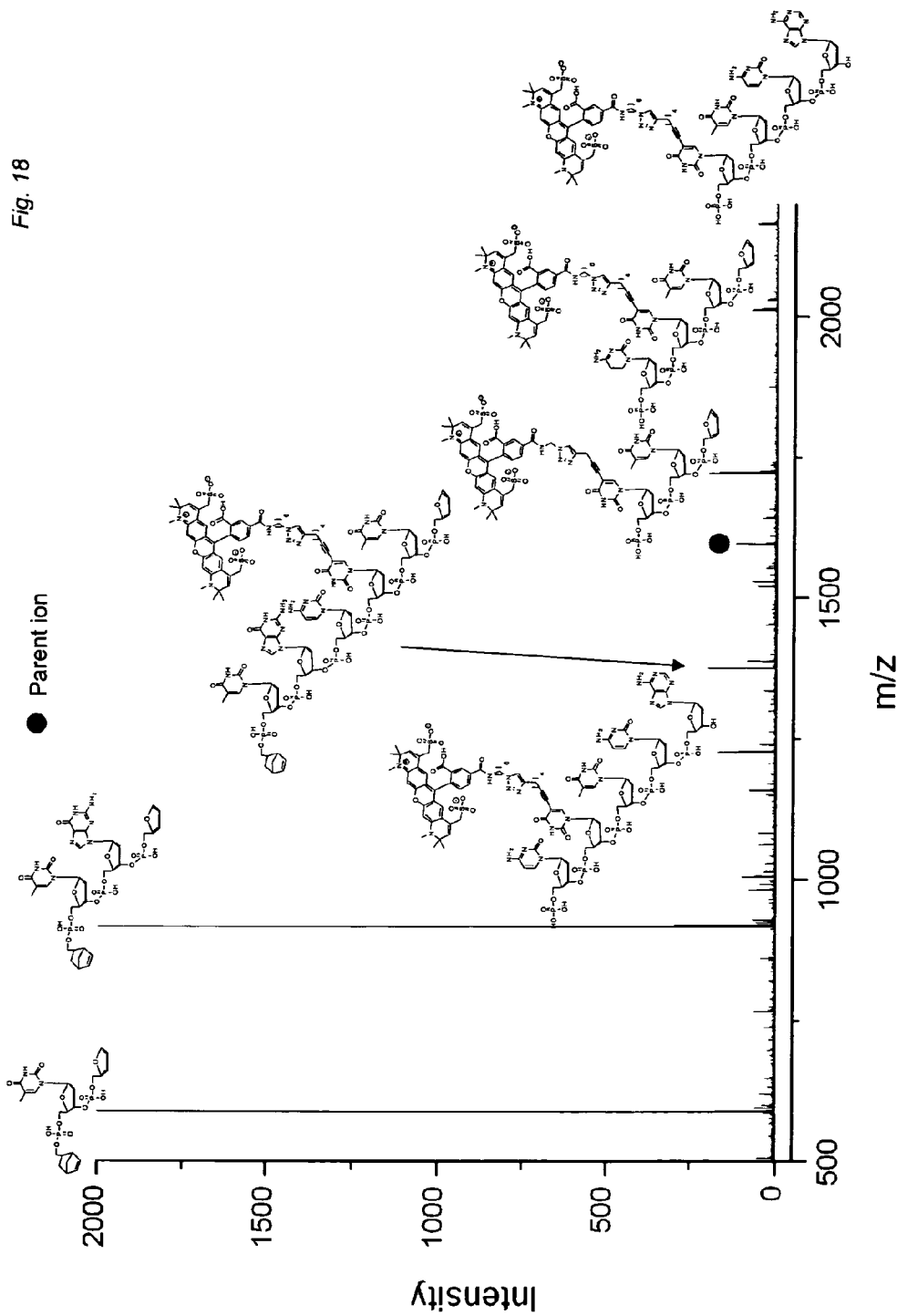
FIG. 18 shows the detailed MSMS spectrum for the double-modified CuAAC ODN1a reaction product.

For the MSMS-measurements, double-charged peak at 1595 (CuAAC ODN1a) was taken as parent ion, wherein the settings for the MSMS-measurements were the following: CuAAC ODN1a (isolation ion: 1595; isolation width: 10; collision energy: 40 eV; acquisition factor: 100). As the same fragmentation scheme was obtained for CuAAC ODN1a and CuAAC ODN2a reaction products, only MSMS-spectrum and fragmentation pattern of CuAAC ODN1a reaction product is described in detail (FIG. 17 and FIG. 18).

A summary of the MSMS analysis of the CuAAC ODN1a reaction product is shown in Table 8.

TABLE 8

Results of the MSMS analysis of the CuAAC ODN1a reaction product

| Fragment | Molecular formula | Mass calculated | Mass measured |
|---|---|---|---|
| 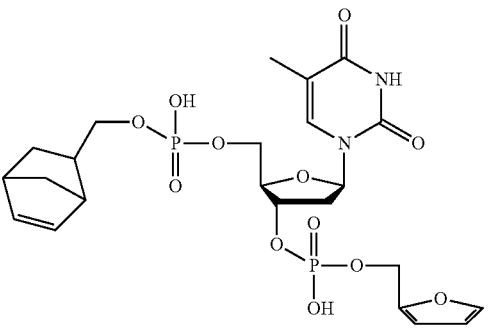 | $[C_{23}H_{30}N_2O_{12}P_2—H]^-$ | 587.1201 | 587.1204 |
| 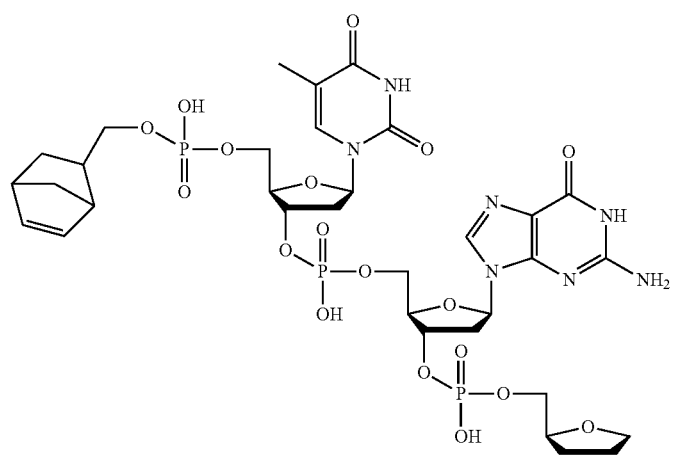 | $[C_{33}H_{42}N_7O_{18}P_3—H]^-$ | 916.1726 | 916.1730 |

TABLE 8-continued
Results of the MSMS analysis of the CuAAC ODN1a reaction product
| Fragment | Molecular formula | Mass calculated | Mass measured |
|---|---|---|---|
| 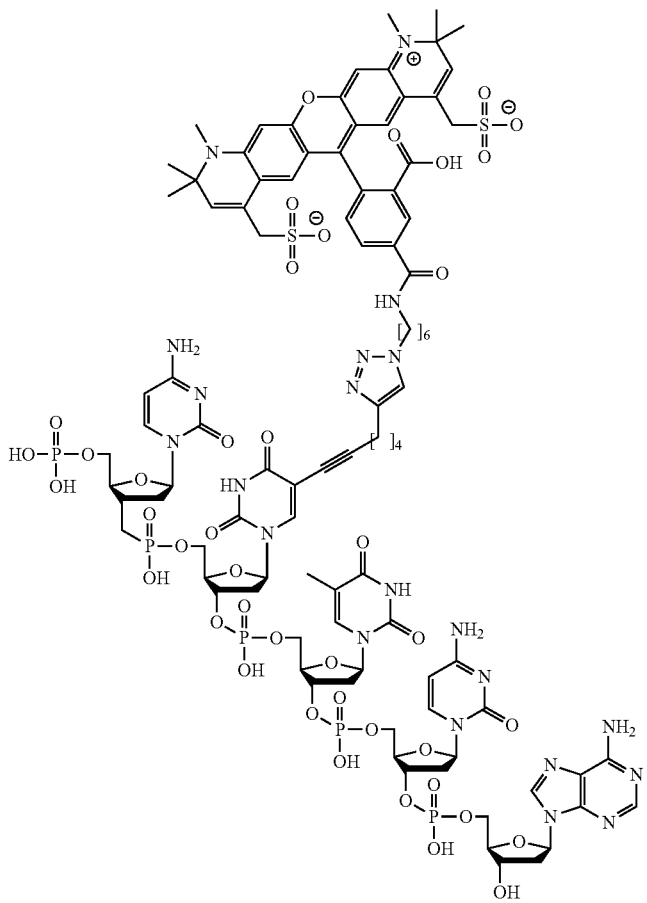 | $[C_{96}H_{116}N_{21}O_{42}P_5S_2-2H]^{2-}$ | 1225.7780 | 1225.7785 |

TABLE 8-continued

Results of the MSMS analysis of the CuAAC ODN1a reaction product

| Fragment | Molecular formula | Mass calculated | Mass measured |
| --- | --- | --- | --- |
| | $[C_{110}H_{132}N_{20}O_{48}P_6S_2-2H]^{2-}$ | 1374.3112 | 1374.3076 |

TABLE 8-continued
Results of the MSMS analysis of the CuAAC ODN1a reaction product
| Fragment | Molecular formula | Mass calculated | Mass measured |
|---|---|---|---|
| 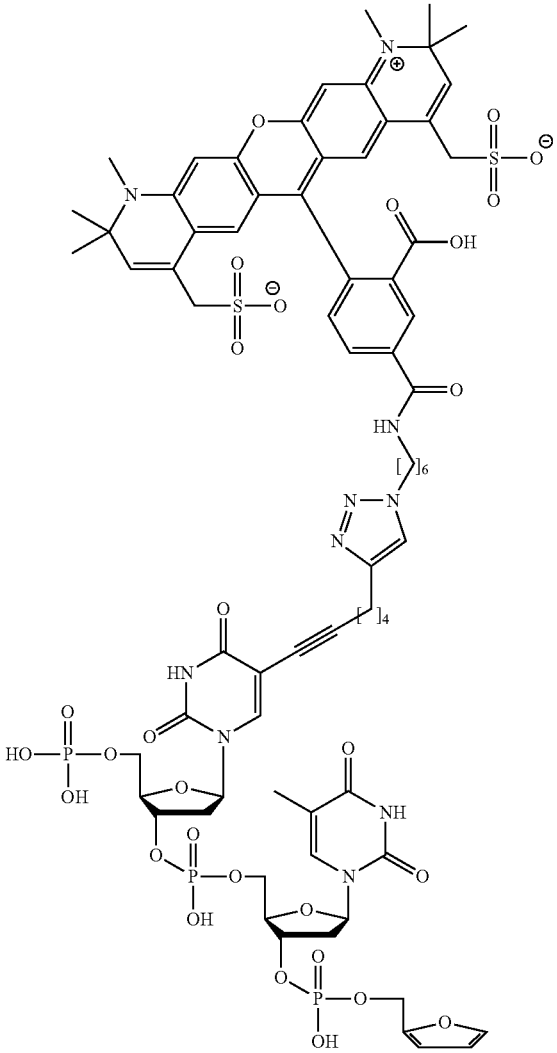 | $[C_{73}H_{85}N_{10}O_{29}P_3S_2-H]^-$ | 1721.4065 | 1721.4060 |

TABLE 8-continued

Results of the MSMS analysis of the CuAAC ODN1a reaction product

| Fragment | Molecular formula | Mass calculated | Mass measured |
|---|---|---|---|
| (structure) | $[C_{82}H_{97}N_{13}O_{35}P_4S_2-H]^-$ | 2010.4498 | 2010.4529 |
| | $[C_{82}H_{97}N_{13}O_{35}P_4S_2-2H]^{2-}$ | 1005.2238 | 1005.2233 |

TABLE 8-continued

Results of the MSMS analysis of the CuAAC ODN1a reaction product

| Fragment | Molecular formula | Mass calculated | Mass measured |
|---|---|---|---|
| 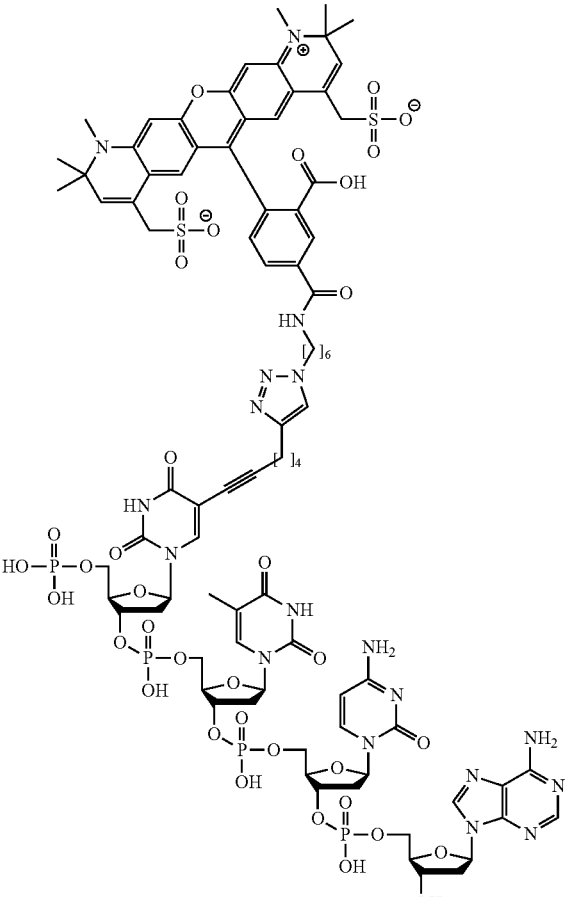 | $[C_{87}H_{104}N_{18}O_{36}P_4S_2-H]^-$ | 2163.5152 | 2163.5180 |

Example 5

LC-MS and/or LC-MSMS Analysis of the One-pot Reaction Product after Simultaneously Performing the DAinv and CuAAC Reactions Using Shorter Oligonucleotides For the analysis of the one-pot reaction product using the shorter oligonucleotides ODN1a and ODN2a after simultaneously performing the DAinv and CuAAC reactions (CuAAC+DAinv), the following pipetting scheme was used as shown in Table 9.

TABLE 9

Pipetting scheme simultaneously performing the DAinv and CuAAC reactions

| | | Stock concentration | Final concentration |
|---|---|---|---|
| 3.1 μl | Oligonucleotide | 80 μM | 9 μM |
| 19.7 μl | NaOAc buffer pH 4.79 | | |

TABLE 9-continued

Pipetting scheme simultaneously performing the DAinv and CuAAC reactions

| | | Stock concentration | Final concentration |
|---|---|---|---|
| 1 μl | Alexafluorazide | 1 mM in DMSO | 36 μM |
| 0.5 μl | CuSO$_4$ | 50 mM | 900 μM |
| 2.5 μl | THPTA | 50 mM | 4.5 mM |
| 1 μl | p-hydrochinone and sodiumascorbate, respectively | 500 mM | 18 mM |
| 1 μl | dansyl-tetrazine | 800 μM in dioxane | 29 μM |

Compared to the pipetting scheme as shown in Table 6, the reducing agent Na-ascorbate has been replaced by p-hydrochinone for DARinv/CuAAC on ODN1a and ODN1b. Alternatively, DARinv/CuAAC reaction can be performed stepwise, by first incubating with tetrazine (DARinv) followed by CuAAC reaction (Na-ascorbate as reducing agent). For trans-cyclooctene modified ODNs the double labeled product could be obtained in simultaneous one-pot reactions by using Na-ascorbate as reducing agent.

Stock solutions were combined in the above order whereas $CuSO_4$ and THPTA were mixed before addition to the reaction mixture. After incubation for one hour at room temperature the samples were diluted to 55 µl and injected into LC-MS.

Figure 19:
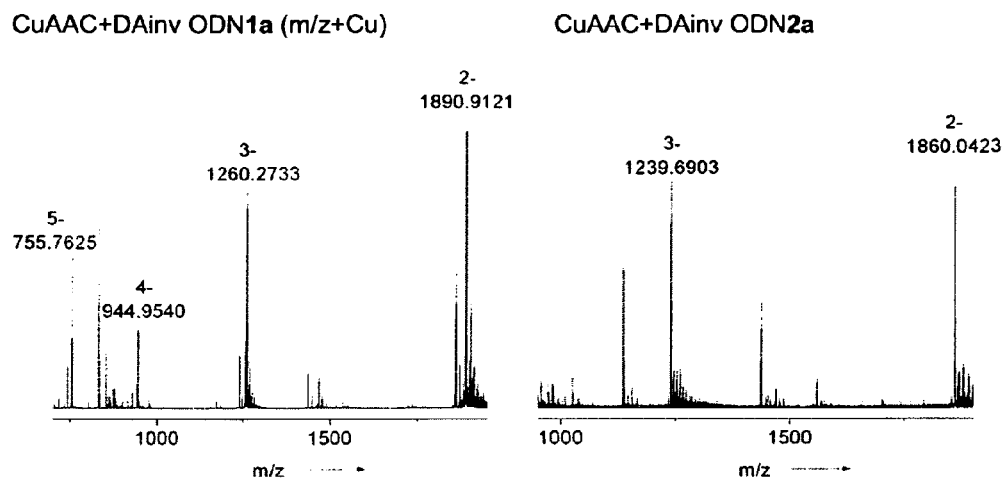
FIG. 19 shows MS spectra of the double-modified CuAAC+DAinv ODN1a and CuAAC+DAinv ODN2a reaction products.

The gradient used for LC-MS analysis was an increase from 20% methanol to 50% methanol over 30 min. MS spectra of the CuAAC+DAinv ODN1a and CuAAC+DAinv ODN2a reaction products are shown in FIG. 19, wherein the MS results, i.e. [M] calculated and [M] deconvoluted are shown in Table 10.

TABLE 10

LC-MS analysis of the CuAAC + DAinv ODN1a and CuAAC + DAinv ODN2a reaction products

| ODN | [M + Cu] calculated | [M + Cu] deconvoluted | Deviation [ppm] |
|---|---|---|---|
| ODN1a | 3782.8419 | 3782.8545 | 3.3 |
| ODN2a | 3784.8576 | 3784.8669 | 2.4 |

Figure 20:
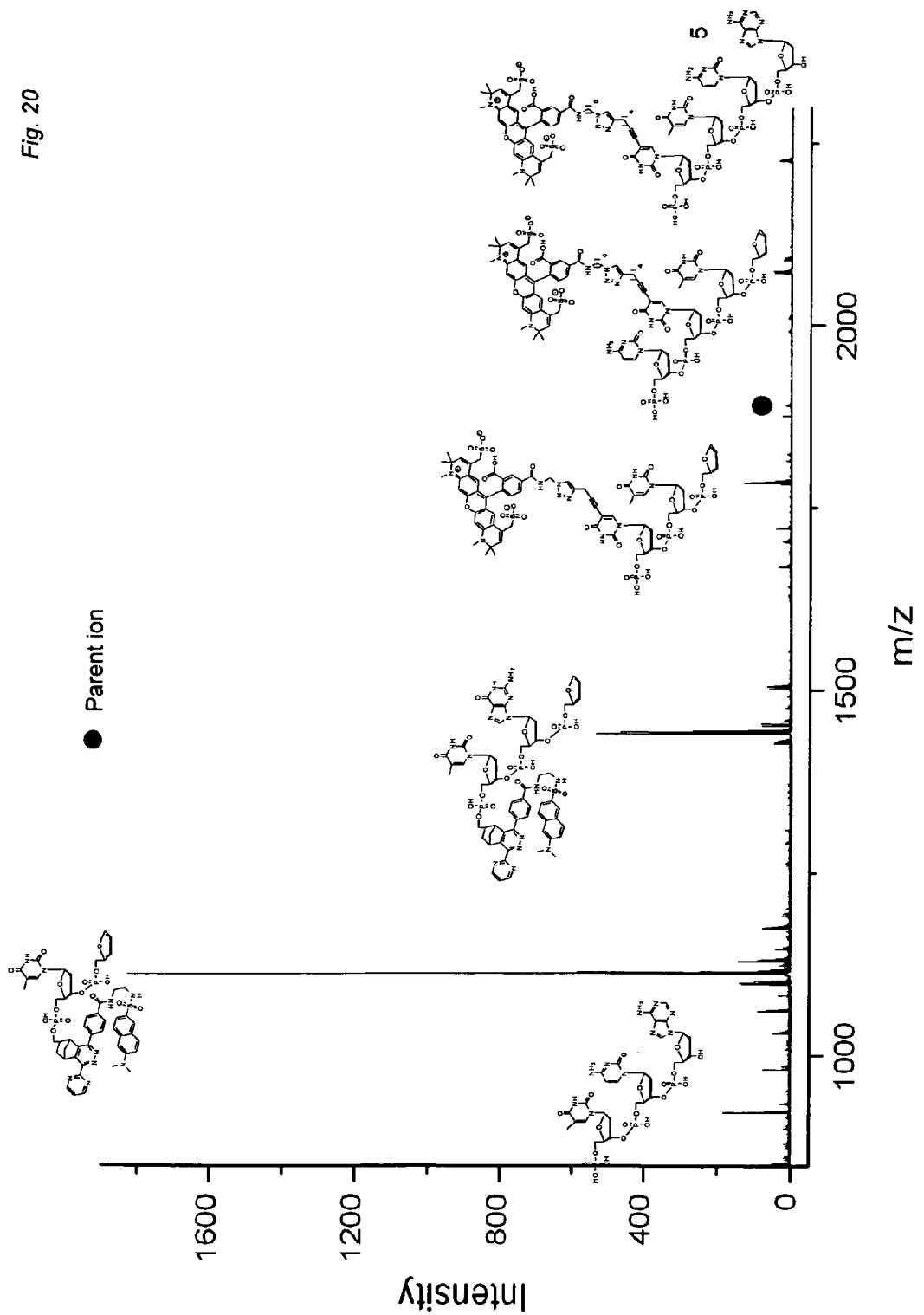
FIG. 20 shows the MSMS spectrum of the double-modified CuAAC+DAinv ODN1a reaction product.

For the MSMS-measurements, double-charged peak at 1890 (CuAAC+DAinv ODN1a) was taken as parent ion, wherein the settings for the MSMS-measurements were the following: CuAAC+DAinv ODN1a (isolation ion: 1890; isolation width: 10; collision energy: 50 eV; acquisition factor: 100). As the same fragmentation scheme was obtained for CuAAC+DAinv ODN1a and CuAAC+DAinv ODN2a reaction products, only MSMS-spectrum and fragmentation pattern of CuAAC+DAinv ODN1a reaction product is described in detail (FIG. 20).

A summary of the MSMS analysis of the CuAAC+DAinv ODN1a reaction product is shown in Table 11.

TABLE 11

Results of the MSMS analysis of the CuAAC + DAinv ODN1a reaction product

| Fragment | Molecular formula | Mass calculated | Mass measured |
|---|---|---|---|
| 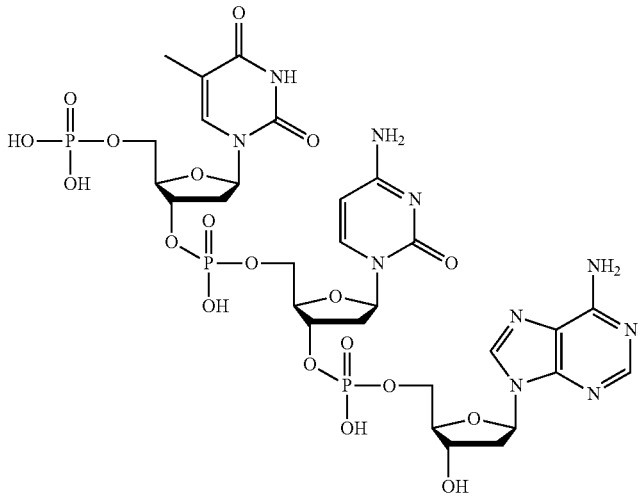 | $[C_{29}H_{39}N_{10}O_{19}P_3-H]^-$ | 923.1533 | 923.1503 |
| 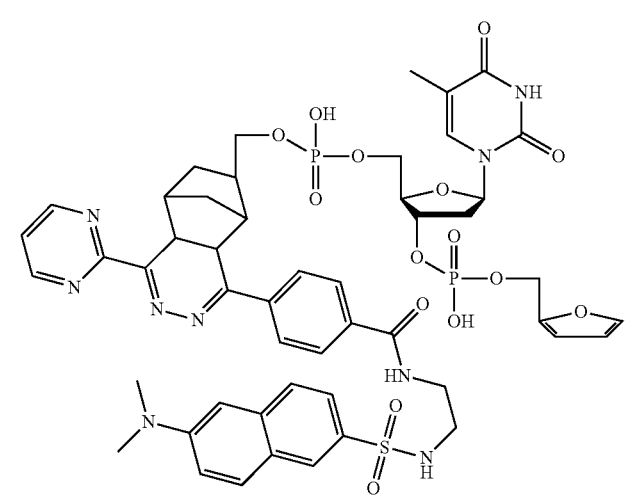 | $[C_{50}H_{53}N_9O_{15}P_2S-H]^-$ | 1112.2784 | 1112.2743 |

TABLE 11-continued

Results of the MSMS analysis of the CuAAC + DAinv ODN1a reaction product

| Fragment | Molecular formula | Mass calculated | Mass measured |
|---|---|---|---|
| | [C$_{60}$H$_{65}$N$_{14}$O$_{21}$P$_3$S—H]$^-$ | 1441.3309 | 1441.3259 |
| | [C$_{73}$H$_{85}$N$_{10}$O$_{29}$S$_2$Cu—2H]$^-$ | 1783.3283 | 1783.3215 |

TABLE 11-continued

Results of the MSMS analysis of the CuAAC + DAinv ODN1a reaction product

| Fragment | Molecular formula | Mass calculated | Mass measured |
|---|---|---|---|
| | $[C_{82}H_{97}N_{13}O_{35}P_4S_2Cu-2H]^-$ | 2072.3747 | 2072.3561 |

TABLE 11-continued

Results of the MSMS analysis of the CuAAC + DAinv ODN1a reaction product

| Fragment | Molecular formula | Mass calculated | Mass measured |
|---|---|---|---|
| | $[C_{87}H_{104}N_{18}O_{36}P_4S_2Cu-2H]^-$ | 2225.4397 | 2225.4257 |

SUMMARY OF THE EXAMPLES 1-5

In general, the norbornene as well as the alkyne modification are reactive in DAinv reactions. Nevertheless, it was shown that norbornene does have a higher reactivity caused by higher HOMO (highest occupied molecular orbital) energy (Sauer, J., et al., Eur. J. Org. Chem. 1998: 2885-2896). Thus, to prove the selectivity of the DAinv on norbornene, the double modified oligonucleotides ODN1a and ODN2a were incubated with dansyl-tetrazine for one hour at room temperature. The reaction mixture was either initially submitted to LC-MS or directly submitted to LC-MSMS (Collision energy: 40 eV). Comparison of the fragmentation schemes showed that fragments carrying an alkyne (e.g. m/z=875.1335 and m/z=875.1339) are appearing in the spectrum of ODN1a (FIG. 11) as well as in the spectrum of the DAinv product (FIG. 14). In contrast to that, peaks corresponding to norbornene carrying fragments (e.g. m/z=587.1201 and m/z=916.1726) have been only found in the spectrum of ODN1a (FIG. 11). In contrast to this, new peaks are showing up in the LC-MSMS spectrum of the DAinv reaction product (FIG. 14; m/z=1114.2901 and m/z=1443.3367) corresponding to the DAinv reaction product of fragments at m/z=587.1181 and m/z=916.1701 in the spectrum of ODN1a (FIG. 11). From this follows that the DAinv reaction is only taken place on the norbornene and alkyne is still intact after the reaction. In a next step, selectivity of the CuAAC was examined. ODN1a was therefore incubated with Alexafluorazide, CuSO₄, THPTA and Na-ascorbate for one hour at room temperature. Afterwards the reaction mixture was subjected to LC-MSMS (Collision energy: 40 eV) analysis. The fragmentation scheme of the CuAAC reaction product, i.e. of the click-reaction product (FIG. 17) shows the same peaks (m/z=587.1204 and m/z=916.1730) corresponding to fragments carrying norbornene as in the LC-MSMS spectrum of ODN1a (FIG. 11). Fragments carrying the alkyne modification, however, did disappear in the spectrum of the CuAAC reaction product (FIG. 17). In exchange, peaks corresponding to the CuAAC reaction product of these alkyne modified fragments could be detected (FIG. 17; m/z=1721.4060). In conclusion, the CuAAC is selectively taken place on the alkyne modification whereas the norbornene is not reacting.

Same analysis was done with the trans-cyclooctene modified oligonucleotides ODN2a and ODN4a (same sequence as ODN2a, whereas 4 was coupled at the 5'-position) Therefore same fragmentation schemes were obtained showing that the DAinv is selectively taken place on the trans-cyclooctenol (2 and 3, respectively) and the CuAAC on the alkyne.

Example 6

LC-MS Analysis of the One-pot Reaction Product after Simultaneously Performing the DAinv and CuAAC Reactions Using Longer Oligonucleotides To analyse the selectivity of DAinv and CuAAC on the longer oligonucleotides ODN2a and ODN2b, performance of LC-MSMS studies is no longer the method of choice as fragmentation schemes are becoming quite complicated. Thus, to allow analysis of these oligonucleotides, they were designed in a way that they have a restriction site between the alkyne and dienophile modification. Restriction digest was performed using two different enzymes (Sacl and Ddel), whereas Ddel was showing better results. Therefore Ddel was used for all further experiments.

Thus, for the analysis of the one-pot reaction product using the longer oligonucleotides ODN2a and ODN2b after simultaneously performing the DAinv and CuAAC reactions (CuAAC+DAinv), the same pipetting scheme was used as shown in Table 9 as described for the shorter oligonucleotides. After incubation at room temperature, the reaction mixtures were hybridised to the complementary strand and digested using restriction endonucleoase Ddel (New England Biolabs, 50 Units per 250 pmol of oligonucleotide). After overnight restriction digestion at 37° C., samples were subjected to LC-MS analysis. The gradient used for LC-MS analysis was an increase from 5% methanol to 35% methanol over 30 min.

Figure 21:
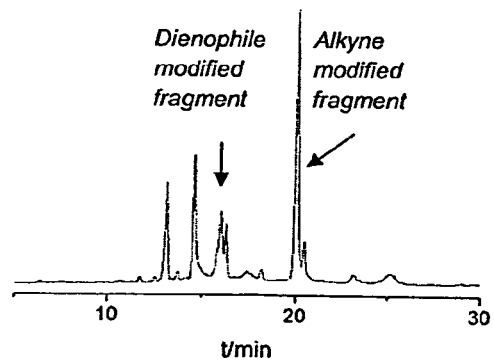
FIG. 21 shows the UV-Chromatogram (LC-MS) of digested ODN1b after hybridisation to the complementary strand using DdeI restriction endonuclease.
Figure 22:
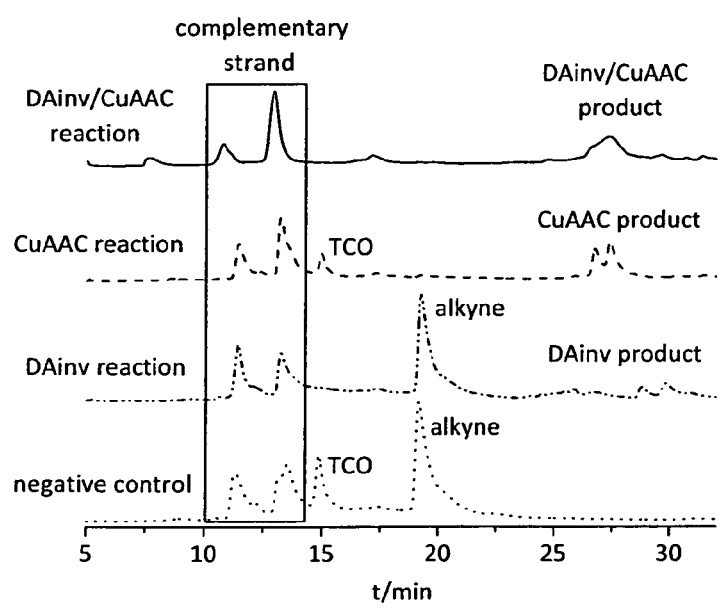
FIG. 22 shows the UV-Chromatogram (LC-MS) of the digested DAinv reaction product of ODN2b after hybridisation to the complementary strand using DdeI restriction endonuclease. LCMS-analysis of DAinv/CuAAC reactions on ODN2b after DdeI restriction digestion. dotted line: negative control w/o reaction, dotted-dashed line: DAinv reaction, dashed line: CuAAC reaction, continuous line: DAinv/CuAAC reaction. TCO: trans-cyclooctenol.

The obtained chromatogram (FIG. 21) showed four different peaks corresponding to the expected digested oligonucleotide fragments. Two of these fragments do either carry the alkyne or the dienophile modification whereas the other peaks belong to the complementary strand hybridist before restriction digestion. With this methodology, DAinv, CuAAC as well as DAinv/CuAAC reaction products were digested and LC-MS analysis performed.

Example 7

Performing the DAinv and CuAAC Reactions Using Longer Oligonucleotides

Example for DARinv/CuAAC on ds233mer Oligonukleotide:
A TCO- and alkyne-modified 233mer oligonucleotide was amplified by PCR using singly modified primers ODN2c-4c (for DAinv, forward primer) and ODN5 (for CuAAC, reverse primer).

The following protocol was used for PCR:
Unmodified (FP, RP) and modified primers ODN2c-4c and ODN5 were incorporated into a long double-stranded DNA by PCR reaction using a plasmid having respective amplifiable insert as template. For PCR reaction, standard protocols were followed using 0.5 µM of each forward and reverse primer, 0.5 mM of each dNTP and 0.02 U/µl Polymerase-X Hybrid DNA polymerase (Roboklon). 52° C. was used as annealing temperature and 26 cycles were performed. PCR yielded clean single products for all different primer combinations which were analyzed on a 2% agarose gel. For removing primers, the PCR product was purified using a Qiagen PCR purification kit.

DARinv/CuAAC-Labelling:
The PCR product was then subjected to either individual DAinv and CuAAC reactions, or to a simultaneous one-pot DAinv/CuAAC reaction using TAMRA-tetrazine and Cy5 azide according to the following protocol:

DAinv reaction: Lyophilized PCR products were dissolved in sodium acetate buffer (pH=4.8, final oligo concentration: 2 µM), TAMRA tetrazine (1. eq. or rather 10eq for negative control) was added and the mixture was incubated for one hour at 37° C.

CuAAC reaction: Lyophilized PCR products were dissolved in sodium acetate buffer (pH=4.8, final oligo concentration: 2 µM), Cy5 azide (250 eq. or rather 500 eq for negative control) a premixed solution of CuSO4/THPTA=1:5 (100 eq. CuSO4) and sodium ascorbate (200 eq.) were added and the mixture was incubated for one hour at 37° C.

DAinv/CuAAC reaction: Lyophilized PCR products were dissolved in sodium acetate buffer (pH=4.8, final oligo concentration: 2 µM), 250 eq. of Cy5 azide, a premixed solution of CuSO4/THPTA=1:5 (100 eq. CuSO4) and sodium ascorbate (200 eq.) were added. To this TAMRA tetrazine (1. eq) was added and the mixture was incubated for one hour at 37° C. Negative control on non-modified PCR product: Same protocol as for DAinv/CuAAC reaction was applied on non-modified PCR product.

Figure 23:
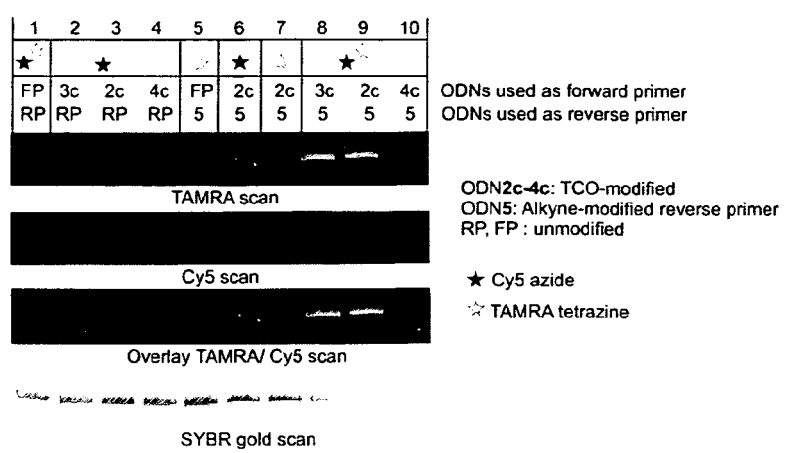
FIG. 23 shows a 15% Denaturing polyacrylamide gel of DAinv/CuAAC labeling reaction on an alkyne/TCO-modified ds233mer PCR-product. 1) negative control incubating non-modified PCR product with TAMRA-tetrazine, Cy5 azide, THPTA, CuSO4 and sodium ascorbate; 2-4) CuAAC on TCO-modified PCR products; 5) DAinv on alkyne-modified PCR product; 6) CuAAC on doubly modified PCR product of ODN2c; 7) DAinv on doubly modified PCR product of ODN2c; 8-10) Concurrent DAinv/CuAAC on doubly modified PCR products of ODN2c-4c. FP and RP are unmodified oligonucleotides having the same nucleotide sequence as ODN2c-4c and ODN5, respectively.

Gel Analysis:
After polyacrylamide gel electrophoretic separation of the reaction mixtures (15% PAGE), the gels were subjected to fluorescence imaging. The TAMRA scan (excitation 532 nm) revealed all products of a reaction with tetrazine, while all azide-derived products were visualized in the Cy5 scan (excitation 633 nm, FIG. 23). A final SYBR gold staining was used for visualization of the reacted as well as non-reacted oligonucleotide bands. For the PCR product based on ODN4c, no DAinv reaction product was observed (FIG. 5, lane 23), likely due to decomposition of the highly reactive bicyclo[6.1.0] nonenyl ring system during PCR caused by multiple heating cycles to 98° C. In contrast, the cyclooctenol-based dienophiles withstand such treatment without problems and CuAAC as well as DAinv products could be detected (FIG. 23, lane 6-9). For doubly labeled PCR products of primers ODN2c and ODN3c, the bands in both scans overlapped exactly, indicating attachment of both dyes to the same macromolecular species (FIG. 5, lane 8-9). We checked for cross-reactivity by incubating the TCO-only modified PCR product with a 500-fold excess of Cy5 azide, CuSO4, THPTA and sodium ascorbate, and also the alkyne-only PCR product with a 10-fold excess of TAMRA-tetrazine. The absolute absence of any faint green or red band in these control experiments even after 1 hour of reaction time demonstrates the selectivity and orthogonality of DARinv and CuAAC towards oligonucleotide functionalization (FIG. 23, lane 2-5).

The invention claimed is:
1. A method for multiple orthogonal labelling of oligonucleotides by simultaneously performing an inverse Diels-Alder reaction and a copper-catalyzed click reaction in one container, the method comprising:
adding a double-modified oligonucleotide comprising at least one dienophile modification and at least one N3-re- active group modification with at least one N3-modified label, and at least one label-modified diene to create a reaction mixture; and incubating the reaction mixture at a pH between 4-7.

2. The method according to claim 1, further comprising the step of adding a copper compound, a stabilizing ligand, and a reducing agent to the reaction mixture.

3. The method according to claim 1, wherein the method is performed between 5-120 min.

4. The method according to claim 1, wherein the method is performed at a temperature between 5-50° C.

5. The method according to claim 1, wherein the at least one N3-modified label and one or more labels of the at least one label-modified diene are molecules containing functional groups and are selected from the group consisting of dyes, radiolabels and affinity tags, wherein the dyes can be selected from the group consisting of fluorescent, luminescent and phosphorescent dyes; wherein the affinity tags are selected from the group consisting of biotin, His-tag, Flag-tag, strep-tag, sugars, lipids, sterols, PEG-linkers, and co-factors; and wherein the radiolabels are selected from the group consisting of radioactive forms of hydrogen, carbon, phosphorous, sulphur, and iodine, including tritium, carbon-11, carbon-14, phosphorous-32, phosphorous-33, sulphur-33, iodine-123, and iodine-125.

6. The method according to claim 1, wherein the method is performed using longer oligonucleotides in a final concentration of about 0.5-15 µM, wherein the longer oligonucleotides have 15-300 nucleotides.

7. The method according to claim 6, wherein a restriction site is additionally synthesized between the $N_3$-reactive group and the dienophile modification, and wherein a restriction digest is performed using restriction enzymes that are selected from the group consisting of SacI and DdeI.

8. The method according to claim 1, wherein in the inverse Diels-Alder reaction, the electron-rich dienophile is selected from the group consisting of a norbornene and frans-cyclooctene.

9. The method according to claim 1, wherein in the inverse Diels-Alder reaction, the label-modified diene is a tetrazine that is selected from the group consisting of a fluorophore-tetrazine and biotin-tetrazine.

10. The method according to claim 1, wherein in the copper-catalyzed click reaction the at least one $N_3$-reactive group is a terminal alkyne moiety.

11. The method according to claim 1, wherein in the copper-catalyzed click reaction the $N_3$-modified label is a label comprising a functional group that is modified with an azide.

12. A method for multiple orthogonal labelling of oligonucleotides by simultaneously performing an inverse Diels-Alder reaction and a copper-catalyzed click reaction, the method comprising:

(a*) providing an oligonucleotide modified by the incorporation of at least one electron-rich dienophile and at least one $N_3$-reactive group;

(b*) providing an electron-deficient diene that is modified with one or more labels;

(c*) providing of an $N_3$-modified label comprising a functional group that is modified with an azide;

(d*) reacting the at least one electron-rich dienophile of step (a*) with the modified electron-deficient diene via an inverse Diels-Alder reaction;

(e*) reacting the at least one $N_3$-reactive group of step (a*) with the $N_3$-modified label via a copper-catalyzed click reaction; and (f*) incubating the reaction mixture at a pH between 4-7.

13. The method according to claim 12, wherein the set of steps (a*), (b*) and (d*) and the set of steps (a*), (c*) and (e*) are simultaneously performed in one container, wherein steps (a*), (b*), (d*) and steps (a*), (c*), (e*) are consecutively performed within the set, respectively.

14. The method of claim 1, wherein the method is performed using shorter oligonucleotides in a final concentration of about 0.5-15 µm, wherein the shorter oligonucleotides have 4-8 olignucleotides.

15. The method of claim 2, wherein the stabilizing agent is TBTA or THPTA.

16. The method of claim 2, wherein the copper compound is a Cu(II) species.

17. The method of claim 2, wherein the reducing agent is p-hydrochinone or sodium ascorbate.

18. The method of claim 3, wherein the method is performed for about 60 minutes.

19. The method of claim 4, wherein the method is performed at 25° C.

20. The method of claim 4, wherein the method is performed at room temperature.

21. The method of claim 5, wherein the dyes are selected from the group consisting of dansyl-, fluorescein-, acridine-, rhodamine-, BODIPY-, and cyanine-based dyes.

22. The method of claim 12, wherein the at least one $N_3$-reactive group is a terminal alkyne moiety.

23. The method of claim 12, wherein the oligonucleotide is modified singly.

24. The method of claim 12, wherein the oligonucleotide is modified multiply.

25. The method of claim 12, wherein the oligonucleotide is modified terminally.

26. The method of claim 12, wherein the oligonucleotide is modified internally.

* * * * *